United States Patent
Franceschini et al.

(10) Patent No.: US 11,872,022 B2
(45) Date of Patent: Jan. 16, 2024

(54) SYSTEM AND METHOD FOR AN OPTICAL BLOOD FLOW MEASUREMENT

(71) Applicant: THE GENERAL HOSPITAL CORPORATION, Boston, MA (US)

(72) Inventors: Maria Angela Franceschini, Charlestown, MA (US); Stefan Carp, Boston, MA (US); Davide Tamborini, Charlestown, MA (US); David Boas, Charlestown, MA (US); Bruce Rosen, Charlestown, MA (US); Megan Blackwell, Charlestown, MA (US); Oleg Shatrovoy, Charlestown, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 525 days.

(21) Appl. No.: 16/970,670

(22) PCT Filed: Feb. 18, 2019

(86) PCT No.: PCT/US2019/018423
§ 371 (c)(1),
(2) Date: Aug. 18, 2020

(87) PCT Pub. No.: WO2019/161336
PCT Pub. Date: Aug. 22, 2019

(65) Prior Publication Data
US 2020/0375476 A1    Dec. 3, 2020

Related U.S. Application Data

(60) Provisional application No. 62/631,927, filed on Feb. 18, 2018.

(51) Int. Cl.
*A61B 5/026* (2006.01)
*G01J 1/44* (2006.01)
(Continued)

(52) U.S. Cl.
CPC .............. *A61B 5/0261* (2013.01); *G01J 1/44* (2013.01); *A61B 2562/0233* (2013.01);
(Continued)

(58) Field of Classification Search
CPC .......... A61B 5/0261; A61B 2562/0233; A61B 5/0075; A61B 5/6868; G01J 1/44;
(Continued)

(56) References Cited

U.S. PATENT DOCUMENTS 9,861,319 B2    1/2018 Yu
10,064,554 B2 *   9/2018 Floyd .................. A61B 5/0075
(Continued)

FOREIGN PATENT DOCUMENTS

CN        102620857 B    11/2013
WO      2015109005 A1     7/2015
(Continued)

OTHER PUBLICATIONS

Baumann N., et al., "Biology of oligodendrocyte and myelin in the mammalian central nervous system," Phys. Rev. 81 (2), 871-927 (2001).
(Continued)

*Primary Examiner* — Seung C Sohn
(74) *Attorney, Agent, or Firm* — Quarles & Brady LLP

(57) ABSTRACT

An apparatus, including: a probe to interface with a surface of a tissue; a light source optically coupled to the probe, the light source directing light of at least 1000 nm into the tissue; a detector optically coupled to the probe, the detector to detect light based on scattering of light from the light source in the tissue, and the detector having a light sensi-
(Continued)

tivity in a range of at least 1000 nm; a processor coupled to the detector, the processor to: receive a signal from the detector corresponding to the detected light from the light source, and determine a blood flow measurement from the region of interest using diffuse correlation spectroscopy based on the signal.

24 Claims, 15 Drawing Sheets

(51) Int. Cl.
  *H01L 31/107* (2006.01)
  *H01L 31/109* (2006.01)
(52) U.S. Cl.
  CPC .  *G01J 2001/448* (2013.01); *G01J 2001/4453* (2013.01); *G01J 2001/4466* (2013.01); *H01L 31/107* (2013.01); *H01L 31/109* (2013.01)
(58) Field of Classification Search
  CPC ....... G01J 2001/4453; G01J 2001/4466; G01J 2001/448; H01L 31/107; H01L 31/109
  See application file for complete search history.

(56) References Cited

U.S. PATENT DOCUMENTS

| | | | | |
|---|---|---|---|---|
| 10,962,414 | B2* | 3/2021 | Durduran | A61B 5/0066 |
| 11,206,990 | B2* | 12/2021 | Lee | A61B 5/0261 |
| 2013/0150245 | A1 | 6/2013 | Smith | |
| 2016/0345880 | A1 | 12/2016 | Nakaji | |

FOREIGN PATENT DOCUMENTS

| | | |
|---|---|---|
| WO | 2016164900 A1 | 10/2016 |
| WO | 2017147539 A1 | 8/2017 |

OTHER PUBLICATIONS

Boas D. A., et al., "Scattering and imaging with diffusing temporal field correlations," Phys. Rev. Lett. 75(9), 1855-1858 (1995).
Boas D. A., et al., "Spatially varying dynamical properties of turbid media probed with diffusing temporal light correlation," J. Opt. Soc. Am. A 14(1), 192-215 (1997).
Bosschaart N., et al. , "A literature review and novel theoretical approach on the optical properties of whole blood," Lasers Med. Sci. 29(2), 453-479 (2014).
Buckley, E.M., et al., 2014. Diffuse correlation spectroscopy for measurement of cerebral blood flow: future prospects. Neurophoton 1, 011009-011009.
Carp S. A., et al. , "Validation of diffuse correlation spectroscopy measurements of rodent cerebral blood flow with simultaneous arterial spin labeling MRI; towards MRI-optical continuous cerebral metabolic monitoring," Biomed. Opt. Express 1(2), 553-565 (2010).
Davie S. N., et al., "Impact of extracranial contamination on regional cerebral oxygen saturation: a comparison of three cerebral oximetry technologies," Anesthesiology 116, 834-840 (2012).
Diop, M., et al. 2011. Calibration of diffuse correlation spectroscopy with a time-resolved near-infrared technique to yield absolute cerebral blood flow measurements. Biomed Opt Express 2, 2068-2081. doi: 10.1364/BOE.2.002068.
Diop, M., et al. 2012. Calibration of diffuse correlation spectroscopy with a time-resolved near-infrared technique to yield absolute cerebral blood flow measurements: errata. Biomed. Opt. Express 3(6), 1476.
Durduran T., et al., "Diffuse correlation spectroscopy for non-invasive, micro-vascular cerebral blood flow measurement," Neuroimage 85, 51-63 (2014).

Durduran T., et al., "Diffuse optical measurement of blood flow, blood oxygenation, and metabolism in a human brain during sensorimotor cortex activation," Opt. Lett. 29(15), 1766-1768 (2004).
Durduran, T., et al., 2010. Optical measurement of cerebral hemodynamics and oxygen metabolism in neonates with congenital heart defects. J Biomed Opt 15, 037004.
Fatouros P. P., Marmarou A., "Use of magnetic resonance imaging for in vivo measurements of water content in human brain: method and normal values," J. Neurosurg. 90, 109-115 (1999).
Gagnon L., et al. , "Double-layer estimation of intra- and extracerebral hemoglobin concentration with a time-resolved system," J. Biomed. Opt. 13(5), 054019 (2008).
Gunadi S., et al. , "Spatial sensitivity and penetration depth of three cerebral oxygenation monitors," Biomed. Opt. Express 5(9), 2896 (2014).
Hale, G.M., et al. 1973. Optical Constants of Water in the 200-nm to 200-microm Wavelength Region. Appl Opt 12, 555-563.
He L., et al. , "Noninvasive continuous optical monitoring of absolute cerebral blood flow in critically ill adults," Neurophotonics 5(04), 045006 (2018).
Highton D., et al., "Noninvasive cerebral oximetry: is there light at the end of the tunnel?" Curr. Opin. Anaesthesiol. 23(5), 576-581 (2010).
International Searching Authority. International Search Report and Written Opinion for application PCT/US2019/018423. dated May 3, 2019.
Jacques S. L., "Optical properties of biological tissues: a review," Phys. Med. Biol. 58(11), R37-R61 (2013).
Jacques, S.L., 2013. Corrigendum: Optical properties of biological tissues: a review. Phys Med Biol 58, 5007-5008.
Jain V., et al. , "Cerebral oxygen metabolism in neonates with congenital heart disease quantified by MRI and optics," J. Cereb. Blood Flow Metab. 34, 380-388 (2014).
Kleiser S., et al. , "Comparison of tissue oximeters on a liquid phantom with adjustable optical properties," Biomed. Opt. Express 7(8), 2973 (2016).
Kobat, D., et al., 2009. Deep tissue multiphoton microscopy using longer wavelength excitation. Opt Express 17, 13354-13364.
Kobat, D., et al. 2011. In vivo two-photon microscopy to 1.6-mm depth in mouse cortex. J Biomed Opt 16, 106014.
Lin, P.-Y., et al. "Non-invasive optical measurement of cerebral metabolism and hemodynamics in infants." JoVE (Journal of Visualized Experiments) 73 (2013): e4379.
Mesquita, R.C., et al. 2011. Direct measurement of tissue blood flow and metabolism with diffuse optics. Philos Transact A Math Phys Eng Sci 369, 4390-4406.
Ohmae E., et al. , "Cerebral hemodynamics evaluation by near-infrared time-resolved spectroscopy: correlation with simultaneous positron emission tomography measurements," Neuroimage 29(3), 697-705 2006.
Okada E., et al. "Near-infrared light propagation in an adult head model II Effect of superficial tissue thickness on the sensitivity of the near-infrared spectroscopy signal," Appl. Opt. 42, 2915-2922 (2003).
Povazay B., et al. , "Three-dimensional optical coherence tomography at 1050 nm versus 800 nm in retinal pathologies: enhanced performance and choroidal penetration in cataract patients," J. Biomed. Opt. 12(4), 041211 (2007).
Prahl S. A., "Tabulated molar extinction coefficient for hemoglobin in water," http://omlc.ogi.edu/spectra/hemoglobin/summary.html (2018). Accessed online at https://web.archive.org/web/20180123074315/http://omlc.org/spectra/hemoglobin/summary.html.
Samra S. K., et al. , "Evaluation of a cerebral oximeter as a monitor of cerebral ischemia during carotid endarterectomy," Anesthesiology 93(4), 964-970 (2000).
Selb, J. J., et al. "Sensitivity of near-infrared spectroscopy and diffuse correlation spectroscopy to brain hemodynamics: simulations and experimental findings during hypercapnia." Neurophotonics 1.1 (2014): 015005.
Sutin, J., et al. "Time-domain diffuse correlation spectroscopy." Optica 3.9 (2016): 1006-1013.

(56) References Cited

OTHER PUBLICATIONS

Svennerholm L., et al. "Changes in weight and compositions of major membrane components of human brain during the span of adult human life of Swedes," Acta Neuropathol. 94(4), 345-352 (1997).
Tamborini D., et al., "Development and characterization of a multidistance and multiwavelength diffuse correlation spectroscopy system," Neurophotonics 5(1), 011015 (2017).
Tamborini D., et al., "Portable system for time-domain diffuse correlation spectroscopy," IEEE Trans. Biomed. Eng. 66(11), 3014-3025 (2019).
Tosh W., et al. "Cerebral oximetry," BJA Educ. 16(12), 417-421 (2016).
Upputuri P. K., et al. "Photoacoustic imaging in the second near-infrared window: a review," J. Biomed. Opt. 24(4), 040901 (2019).
Van Veen R. L. P., et al., "Determination of visible near-IR absorption coefficients of mammalian fat using time- and spatially resolved diffuse reflectance and transmission spectroscopy," J. Biomed. Opt. 10(5), 054004 (2005).
Varma, H. M., et al. "Speckle contrast optical tomography: A new method for deep tissue three-dimensional tomography of blood flow." Biomedical optics express 5.4 (2014): 1275-1289.
Wang, X., et al. 2005. Approximation of Mie scattering parameters in near-infrared tomography of normal breast issue in vivo. J Biomed Opt 10, 051704.
Wilson R. H., et al., "Review of short-wave infrared spectroscopy and imaging methods for biological tissue characterization," J. Biomed. Opt. 20(3), 030901 (2015).
Wray, S., et al. 1988. Characterization of the near infrared absorption spectra of cytochrome aa3 and haemoglobin for the non-invasive monitoring of cerebral oxygenation. Biochim Biophys Acta 933, 184-192.
Yu G., et al., "Validation of diffuse correlation spectroscopy for muscle blood flow with concurrent arterial spin labeled perfusion MRI," Opt. Express 15(3), 1064 (2007).
Yücel M. A., et al., "Functional near infrared spectroscopy: enabling routine functional brain imaging," Curr. Opin. Biomed. Eng. 4, 78-86 (2017).
Zhou C., "In-vivo optical imaging and spectroscopy of cerebral hemodynamics," PhD thesis, University of Pennsylvania (2007). Abstract.
Zhou C., et al., "Diffuse optical monitoring of hemodynamic changes in piglet brain with closed head injury," J. Biomed. Opt. 14(3), 034015 (2009).
Zhou, W., et al. "Highly parallel, interferometric diffusing wave spectroscopy for monitoring cerebral blood flow dynamics." Optica 5.5 (2018): 518-527.
Zijlstra, W., et al. 1983. Molar absorptivities of human hemoglobin in the visible spectral range. J Appl Physiol 54, 1287-1291.
Zirak, P., et al. "Effects of acetazolamide on the micro-and macro-vascular cerebral hemodynamics: a diffuse optical and transcranial doppler ultrasound study." Biomedical optics express 1.5 (2010): 1443-1459.

\* cited by examiner

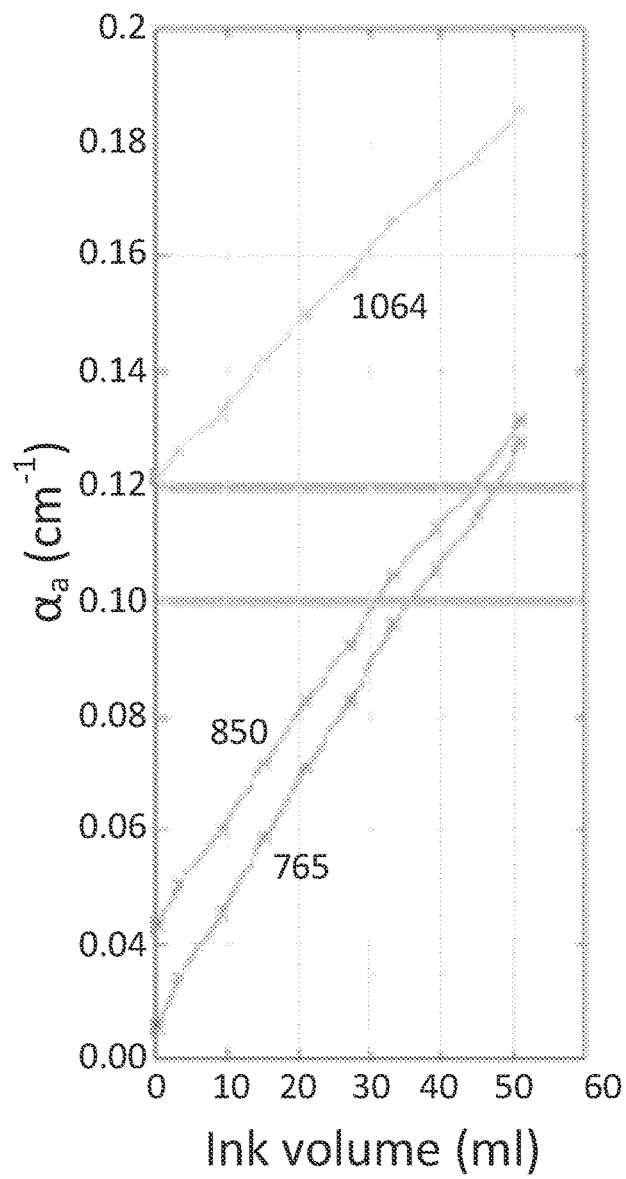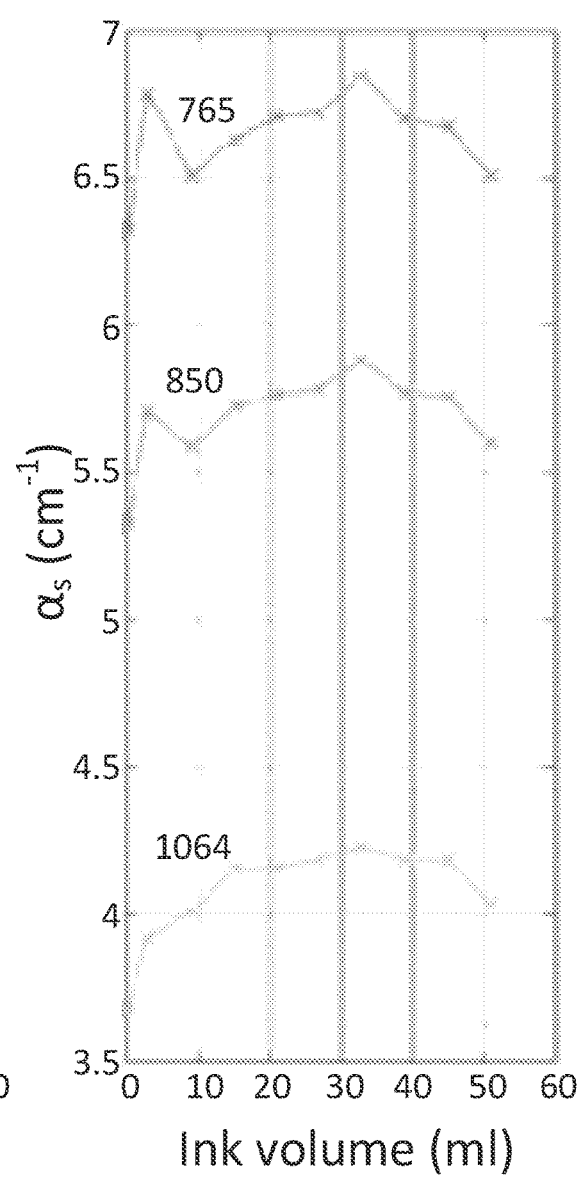
FIG. 7A
FIG. 7B

SYSTEM AND METHOD FOR AN OPTICAL BLOOD FLOW MEASUREMENT

CROSS-REFERENCE TO RELATED APPLICATIONS

This application represents the national stage entry of PCT International Application No. PCT/US2019/018423 filed Feb. 18, 2019, which is based on, claims the benefit of, and claims priority to U.S. Provisional Application No. 62/631,927, filed Feb. 18, 2018, which is hereby incorporated herein by reference in its entirety for all purposes.

STATEMENT REGARDING FEDERALLY SPONSORED RESEARCH

This invention was made with government support under 1R01EB025145 awarded by the National Institutes of Health (NIH) Brain Initiative, RO1NS100750 awarded by the NIH, and Air Force Contracts FA8721-05-C-0002 and FA8702-15-D-0001 awarded by the Assistant Secretary for Defense and Research Engineering. The government has certain rights in the invention.

FIELD OF THE INVENTION

This invention relates generally to methods and systems for obtaining blood flow measurements using diffuse correlation spectroscopy (DCS).

BACKGROUND

Diffuse optical methods have been used to non-invasively quantify hemodynamic parameters in the brain, skeletal muscles, and other tissues. In particular, near-infrared spectroscopy (NIRS) has been used for performing cerebral oximetry clinical applications and functional neuroimaging studies. NIRS employs light in the red and near-infrared spectral region, between 650 and 900 nm, where hemoglobin absorption is orders of magnitude lower than at shorter wavelengths but is nevertheless considerably higher than water absorption. This "optical window" permits light penetration several centimeters into the tissue and provides high sensitivity to hemoglobin concentration changes.

Diffuse correlation spectroscopy (DCS) is another diffuse optical method whose use is rapidly growing and is applied in a range of biomedical applications. In DCS, a tissue of interest is illuminated by coherent near-infrared light, which causes a speckle interference pattern to form after the light multiply scatters though the tissue. As with NIRS, known DCS devices operate at wavelengths between 765-900 nm, which has lower water absorption than at longer IR wavelengths.

Diffuse correlation spectroscopy has been extensively validated against gold standards and its clinical utility in infants has been demonstrated. However, the effectiveness of DCS in measuring parameters such as cerebral blood flow (CBF) has been hampered in the adult population by limited depth penetration and extra-cerebral contamination, limitations which have so far precluded the wide adoption of optical monitoring techniques in health care settings.

SUMMARY OF THE INVENTION

Therefore, there is a need for an improved DCS system which provides a higher/more reliable signal for a given IR exposure with better penetrating depth, to increase sensitivity to brain blood flow and in general to deeper tissues. There is also a need for a DCS system which may be used in conjunction with an NIRS system to provide a simplified system for measuring tissue blood parameters including one or more of blood flow, oxygen saturation, or oxygen consumption.

Exemplary embodiments according to the present disclosure may be provided which generate DCS readings using longer-wavelength IR (e.g. at or above 1000 nm, in a range of 1000-1400 nm, in a range of 1060-1100 nm, and/or at 1700 nm) than has been previously used. DCS measurements made at these longer IR wavelengths have several advantages over known measurements made at relatively short IR and near-IR wavelengths (e.g. in the optical window of 650-900 nm). For example, the photons for DCS illumination at longer IR wavelengths (e.g. longer than or equal to 1000 nm) have less energy per photon and higher ANSI skin exposure limits, permitting more photons to be sent and detected, which improves measurement signal to noise (SNR) for DCS, which is important since DCS is a photon-counting based method. In addition, the photons for DCS illumination at longer IR wavelengths have greater penetration depth and therefore provide increased sensitivity to brain blood flow and in general to deeper tissues since DCS performance for deep tissue measurements is directly impacted by SNR limitations.

Further, a combined system which uses longer-wavelength IR to perform DCS in conjunction with an NIRS system operating in the optical window of 650-900 nm can be made which is simpler and/or has greater efficiency than known combined systems. By selecting suitable illumination wavelengths and detector technologies for each of the DCS and NIRS modalities, the combined system would be simplified and have increased efficiency by not requiring the use of wavelength filters in front of each detector to block the illumination from the other modality.

Thus, the disclosed embodiments overcome one or more of the limitations of the techniques known in the art described above.

In one exemplary embodiment, an apparatus, including: a probe to interface with a surface of a tissue; a light source optically coupled to the probe, the light source directing light of at least 1000 nm into the tissue; a detector optically coupled to the probe, the detector to detect light based on scattering of light from the light source in the tissue, and the detector having a light sensitivity in a range of at least 1000 nm; a processor coupled to the detector, the processor to: receive a signal from the detector corresponding to the detected light from the light source, and determine a blood flow measurement from the region of interest using diffuse correlation spectroscopy based on the signal.

In another exemplary embodiment, an apparatus, including: a probe to interface with a surface of a tissue; a first light source optically coupled to the probe, the first light source providing light of up to 900 nm into the tissue; a second light source optically coupled to the probe, the second light source providing light of at least 1000 nm into the tissue; a first detector optically coupled to the probe, the first detector to detect light scattered in the tissue from the first light source, and the first detector having a light sensitivity in a range of up to 900 nm; a second detector optically coupled to the probe, the second detector to detect light scattered in the tissue from the second light source, and the second detector having a light sensitivity in a range of at least 1000 nm; and a processor coupled to the first detector and the second detector, the processor to: receive a first signal from the first detector corresponding to the detected light from the first light source, receive a second signal from the second detector corresponding to the detected light from the second light source, and determine a blood flow measurement from the region of interest based on the first signal and the second signal.

In yet another exemplary embodiment, a method, including: directing, using a light source, light of at least 1000 nm into a tissue, the light source optically coupled to a probe, the probe interfaced with a surface of the tissue; detecting, using a detector, light based on scattering of light from the light source in the tissue, the detector optically coupled to the probe, and the detector having a light sensitivity in a range of at least 1000 nm; receiving, by a processor, a signal from the detector corresponding to the detected light from the light source; and determining, by the processor, a blood flow measurement from the region of interest using diffuse correlation spectroscopy based on the signal.

In still another exemplary embodiment, a method, including: directing, using a first light source, light of up to 900 nm into a tissue, the first light source optically coupled to a probe, the probe interfaced with a surface of the tissue; directing, using a second light source, light of at least 1000 nm into the tissue, the second light source optically coupled to the probe, the probe interfaced with a surface of the tissue; detecting, using a first detector, light based on scattering of light from the first light source in the tissue, the first detector optically coupled to the probe, and the first detector having a light sensitivity in a range of up to 900 nm; detecting, using a second detector, light based on scattering of light from the second light source in the tissue, the second detector optically coupled to the probe, and the second detector having a light sensitivity in a range of at least 1000 nm; receiving, by a processor, a first signal from the first detector corresponding to the detected light from the first light source; receiving, by the processor, a second signal from the second detector corresponding to the detected light from the second light source; and determining, by the processor, a blood flow measurement from the region of interest based on the first signal and the second signal.

In yet another embodiment, an apparatus, including: a probe to interface with a surface of a tissue; a light source optically coupled to the probe, the light source directing light of at least 1000 nm into the tissue; and a detector optically coupled to the probe, the detector to detect light based on scattering of light from the light source in the tissue, and the detector having a light sensitivity in a range of at least 1000 nm.

BRIEF DESCRIPTION OF THE DRAWINGS

The foregoing features of this invention, as well as the invention itself, may be more fully understood from the following description of the drawings in which:

FIG. 3A shows a combined system for obtaining DCS and NIRS measurements from a tissue, while

FIGS. 7A, 7B, 7C, and 7D show the results of using a DCS system with liquid phantoms based on ink titrations;

DETAILED DESCRIPTION

Figure 1A:
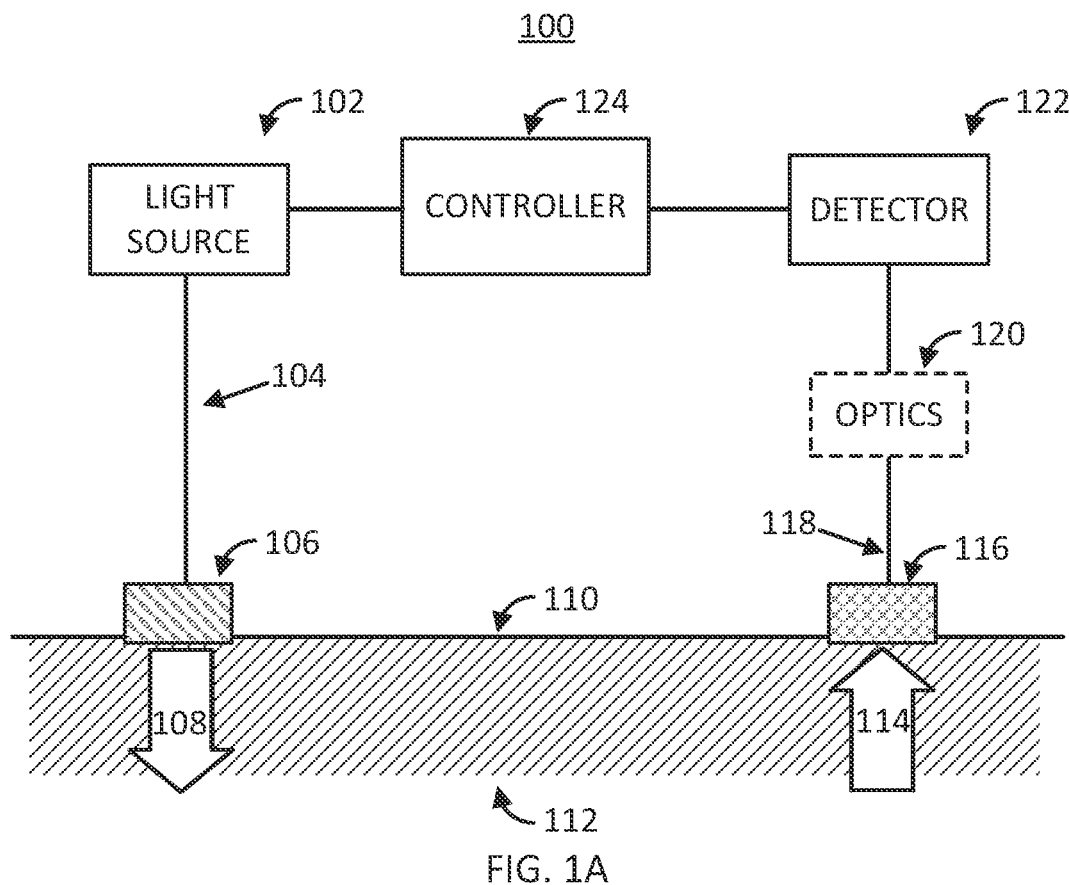
FIG. 1A shows a diagram of an embodiment of a system for obtaining DCS measurements from a tissue.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Embodiments referenced as "comprising", "including", or "having" certain elements are also contemplated as "consisting essentially of and "consisting of those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive, so recitation of a value of between 1 and 10 includes the values 1 and 10. Disclosure of multiple alternative ranges having different maximum and/or minimum values contemplates all combinations of the maximum and minimum values disclosed therein. For example, recitation of a value of between 1 and 10 or between 2 and 9 contemplates a value of between 1 and 9 or between 2 and 10 in addition to the positively recited values, unless explicitly stated to the contrary.

The present invention provides apparatus and methods for performing diffuse correlation spectroscopy (DCS) which may provide one or more of a system having higher performance, efficiency, reduced cost, and/or reduced complexity than other systems. Prior systems (some of which have combined technologies for performing NIRS and DCS measurements into a single system) have confined the measurements to the "optical window" of 650-900 nm in order to utilize detector technologies such as silicon-based avalanche photodiodes (which lose sensitivity at wavelengths above 900 nm) and to avoid regions of the spectrum (generally above 900 nm) having drawbacks such as a 10-fold increase in water absorption.

The presently disclosed system, on the other hand, uses input light having a wavelength of 1000 nm or greater to perform DCS measurements. As will be discussed further below, the present system for performing DCS with longer IR wavelength light unexpectedly provides a stronger signal and higher efficiency than performing DCS with shorter IR wavelength light due to several advantages, namely, that longer IR light provides lower effective attenuation, higher maximum permissible exposure (MPE), and more photons per unit energy. Specifically, by illuminating with light at 1064 nm one ends up with ~10 times more photons at the DCS detector than at 765 nm, which is a considerable gain since the number of photons directly impacts the measurement signal to noise ratio (SNR).

In particular embodiments in which the longer IR wavelength DCS system is used in combination with an NIRS system based on the 650-900 nm optical window, the combination has advantages over a combination in which both modalities use light confined to the shorter IR optical window. That is, since both NIRS and DCS measurements are performed within the same wavelength range, it is necessary on such systems to include wavelength filters (e.g. bandpass, low pass, high pass) in front of the detectors to block the light from the other modality (e.g. in front of the DCS detector to block NIRS light or vice versa), particularly if the NIRS and DCS measurements are to be performed simultaneously. However, in addition to increasing the complexity and cost of the system, the use of such filters introduces signal losses which then reduce the overall efficiency of the measurements for both the NIRS and DCS modalities.

Thus, a combined system which brings together the presently disclosed longer IR wavelength DCS system with a known shorter IR wavelength NIRS system addresses one or more of these drawbacks by providing a matched set of light sources and detectors for performing NIRS and DCS (e.g. simultaneously) without requiring wavelength filters with either detector. In various embodiments, NIRS measurements may be performed using input light having wavelengths in a range of less than 1000 nm, and more particularly in the optical window range of 650-900 nm and with detectors having a sensitivity range of less than 1050 nm, and in particular a range of up to 900 nm (e.g. photomultiplier tubes) or a range of up to 1050 nm (e.g. silicon photodiodes). In certain embodiments, DCS measurements may be performed using input light having wavelengths in a range of at least 1000 nm, in a range of 1000-1400 nm, and in particular in a range of 1060-1100 nm, and in some embodiments DCS measurements may be performed using input light having wavelengths of about 1700 nm. The DCS measurements may be performed using a detector having a sensitivity range of at least 1000 nm, and in particular in a range of 1000-1700 nm.

Diffuse Correlation Spectroscopy (DCS) is an established optical modality which enables non-invasive measurements of blood flow in deep tissue. Similar to Near-Infrared Spectroscopy (NIRS), DCS generally has been performed using red and near-infrared light (650-900 nm) to interrogate biological tissues. However, instead of quantifying hemoglobin concentration and oxygenation from the measure of light attenuation as in NIRS, DCS instead quantifies an index of blood flow ($BF_i$) by measuring the light intensity temporal fluctuations generated by the dynamic scattering of moving red blood cells. Disclosed herein are embodiments in which DCS measurements are performed using longer wavelengths than have been used before for obtaining DCS measurements and longer than the wavelengths typically used by NIRS. In particular, obtaining DCS measurements using light with a longer wavelength such as 1064 nm provides higher depth penetration and greater light throughput than with the shorter wavelengths used previously for DCS and generally used for NIRS.

DCS may be applied in a range of biomedical applications. In DCS, a tissue of interest (e.g. brain tissue) is illuminated by coherent near-infrared light, which causes a speckle interference pattern to form after the light multiply scatters though the tissue. Dynamic scattering of the light by moving red blood cells causes the speckle pattern to fluctuate rapidly. These fluctuations are typically detected 2 to 3 cm away from the source (typically moving through the tissue in an arc) and are quantified by measuring the temporal intensity autocorrelation curve of a single speckle. The decay of the autocorrelation curve is fit with the solution of the correlation diffusion equation to obtain an index of blood flow ($BF_i$) in units of $cm^2/s$. Although the units of $BF_i$ are not the conventional units of ml/min/100 g tissue for perfusion, $BF_i$ is nevertheless reliably proportional to absolute flow, as demonstrated against "gold standards" such as arterial spin-labeled MRI, fluorescent microspheres, bolus tracking time-domain NIRS, and phase-encoded velocity mapping MRI.

Analogous to NIRS, current DCS devices operate at wavelengths between 765-850 nm. However, while NIRS measurements are performed using shorter-wavelength IR and near-IR in order to maximize hemoglobin contrast, the contrast mechanism of DCS relies on dynamic scattering of red blood cells and not on hemoglobin absorption. Thus, it may be advantageous when performing DCS to use longer IR wavelengths for which both the effective attenuation coefficient, $\mu_{eff}$, and the energy carried by the photons are lower. Accordingly, in various embodiments DCS measurements may be made using light at longer IR wavelengths (e.g. at or above 1000 nm, at 1700 nm, or in ranges of 1000-1400 nm or 1060-1100 nm). In particular embodiments, DCS measurements are made using light of 1064 nm and the results of such measurements are compared to DCS measurements made using light at 765 and 850 nm.

A diagram of an embodiment of a system 100 for obtaining DCS measurements from a tissue 112 is shown in FIG. 1A. In general, the system includes a light source 102 (emitting light 108 into the tissue 112) and a detector 122 (detecting light 114 from the tissue 112) coupled to a controller 124, both of which are optically coupled to a probe 110, where the probe is designed to be placed near or on the surface (e.g. skin) of the tissue 112 from which measurements are to be obtained. The light source 102 may include one or more sources and may provide light having one or more wavelengths, either as discrete wavelengths or a continuum of wavelengths. The light source 102 may be coupled 106 to the probe 110 using a fiber optic or other suitable optical coupling 104. Such a system 100 may be used to perform various implementations of DCS including CW-DCS, TD-DCS, interferometric DCS (iDCS and iDWS), heterodyne DCS, multi-speckle DCS, and/or acousto-optic modulated DCS. In various embodiments, DCS implementations may be known as diffusing wave spectroscopy, speckle contrast optical tomography, and/or speckle contrast diffuse correlation tomography.

Figure 1B:
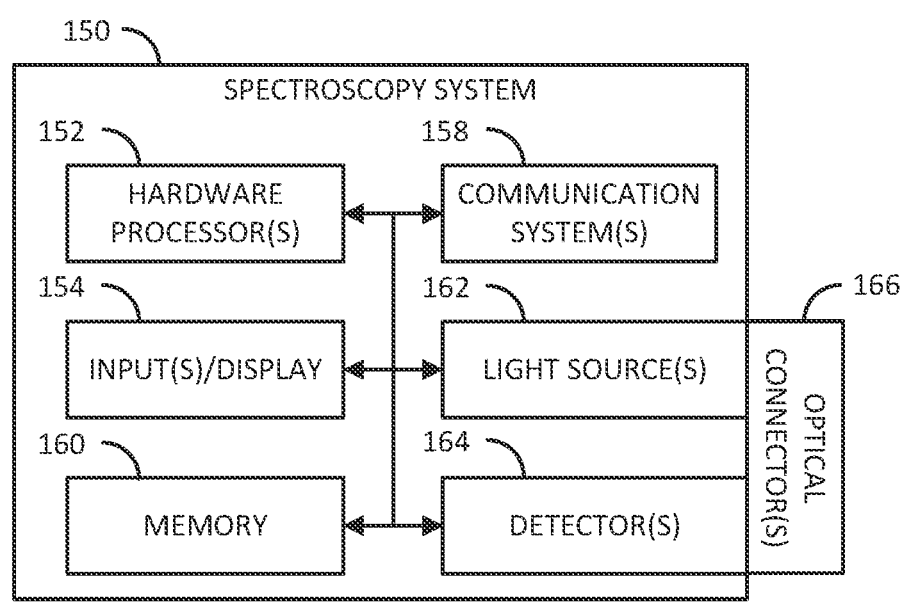
FIG. 1B shows a diagram of a spectroscopy system that can be used with the system of FIG. 1A.

FIG. 1B shows an example 150 of hardware that can be used to implement a spectroscopy system that can be used in connection with some embodiments of the invention in accordance with some embodiments of the disclosed subject matter. As shown in FIG. 1B, in some embodiments, spectroscopy system 150 can include a hardware processor 152, a user interface and/or display 154, one or more communication systems 158, memory 160, one or more light sources 162 (such as light source 102), one or more light detectors 164 (such as detector 122), and/or one or more optical connectors 166. In some embodiments, hardware processor 152 can be any suitable hardware processor or combination of processors, such as a central processing unit (CPU), a graphics processing unit (GPU), a microcontroller (MCU), a field programmable gate array (FPGA), an application-specific integrated circuit (ASIC), a dedicated image processor, etc. In some embodiments, input(s) and/or display 154 can include any suitable display device(s), such as a computer monitor, a touchscreen, a television, etc., and/or input devices and/or sensors that can be used to receive user input, such as a keyboard, one or more physical buttons with dedicated functions, one or more physical buttons with software programmable functions, a mouse, a touchscreen, a microphone, a gaze tracking system, motion sensors, etc.

In some embodiments, communications systems 158 can include any suitable hardware, firmware, and/or software for communicating information over a communication network and/or any other suitable communication networks. For example, communications systems 158 can include one or more transceivers, one or more communication chips and/or chip sets, etc. In a more particular example, communications systems 158 can include hardware, firmware and/or software that can be used to establish a Wi-Fi connection, a Bluetooth connection, a cellular connection, an Ethernet connection, an optical connection, etc.

In some embodiments, the communication network can be any suitable communication network or combination of communication networks. For example, the communication network can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, the communication network can be a local area network, a wide area network, a public network (e.g., the Internet), a private or semi-private network (e.g., a corporate or university intranet), any other suitable type of network, or any suitable combination of networks. Communications links between spectroscopy system and the communication network can each be any suitable communications link or combination of communications links, such as wired links, fiber optic links, Wi-Fi links, Bluetooth links, cellular links, etc.

In some embodiments, memory 160 can include any suitable storage device or devices that can be used to store instructions, values, etc., that can be used, for example, by hardware processor 152 to process image data generated by one or more optical detectors, to present content using input(s)/display 154, to communicate with an external computing device via communications system(s) 158, etc. Memory 160 can include any suitable volatile memory, non-volatile memory, storage, any other suitable type of storage medium, or any suitable combination thereof. For example, memory 160 can include RAM, ROM, EEPROM, one or more flash drives, one or more hard disks, one or more solid state drives, one or more optical drives, etc. In some embodiments, memory 160 can have encoded thereon a computer program for controlling operation of spectroscopy system 150. In some such embodiments, hardware processor 152 can execute at least a portion of the computer program to control one or more light sources and/or detectors, to generate data and/or calculate values (e.g., a value indicative of blood flow, a value indicative of blood oxygenation, etc.), transmit and/or receive information to/from a computing device, etc.

In some embodiments, spectroscopy system 150 can include one or more light sources 162, such as narrow band light sources (e.g., a laser or light emitting diode with a center frequency of 1064 nm, etc.). Additionally, in some embodiments, light sources 162 can be associated with one or more filters.

In some embodiments, spectroscopy system 150 can include one or more light detectors 154, such as one or more single photon avalanche diodes (SPADs), one or more photomultiplier tubes, one or more photodiodes, and/or one or more image sensors (e.g., a CCD image sensor, a CMOS image sensor). For example, in some embodiments, detectors 164 can include one or more detectors configured to detect light at specific wavelengths (e.g., using filters, using timing signals, using optics to guide light of different wavelengths to different portions of the detector(s), etc.).

In some embodiments, spectroscopy system 150 can include one or more optical connectors 166. For example, such optical connectors can be fiber optic connectors configured to form an optical connection between light source(s) 162 and/or detector 164 and an optical fiber (e.g., as part of a fiber optic cable).

In particular embodiments, the light source 102 may include a long coherence length laser (e.g. a source with sufficient coherence to generate interference speckles) that produces light having one or more wavelengths of at least 1000 nm, about 1700 nm, in a range of 1000-1400 nm, or in a range of 1060-1100 nm. In a certain embodiment, the light source is a long coherence length laser that produces light of 1064 nm (e.g. a 200 mW 1064 nm single longitudinal mode long coherence length laser source, Crystalaser CL1064-200-S), which, as discussed below, is especially advantageous for performing DCS measurements. As discussed further below, a source which outputs light in the 1060-1100 nm range and in particular at 1064 nm provides a number of advantages for performing DCS measurements, due in part to a local minimum of water absorption in this wavelength range. In general, a long coherence length laser in the context of DCS context may mean a coherence length that is longer than the difference between the shortest and the longest paths photons might take to arrive at the same exit location (speckle). In certain embodiments, long coherence length may encompass a range of lengths at which speckle contrast can be detected (i.e. interference fringes may be detectable), from as little as lengths of less than a millimeter to tens of centimeters to several meters, which may in some embodiments depend on details of the particular setup that is used. In various embodiments, a long coherence length laser may include a light source having non-negligible coherence and/or a light source having sufficient coherence to generate detectable speckle fluctuations.

The detector 122 may be a point detector or an area detector and may include one or more technologies such as photomultiplier tubes (PMT), superconducting nanowires, cameras (e.g. fast, sensitive CMOS cameras), avalanche photodiodes (APD) or SPADs (Single Photon Avalanche Photodiodes), and/or photodiode arrays made using a variety of photoactive materials (e.g. Si, InP, InGaAs, Ge, PbS, Se, etc.), which may depend in part on the particular implementation of DCS (see: WO 2016/164900 to Sutin et al.; WO 2015/109005 to Nakaji et al.; Zhou et al. Optica 5, 518-527, 2018; Sutin et al. Optica 3, 1006-1013, 2016; Varma et al., Biomed. Opt. Express, 5(4): 1275-1289 (2014) (camera-based detection of speckle pattern); each of which is incorporated by reference in its entirety). In one particular embodiment, the detector may be based on InP/InGaAs SPAD arrays which have high efficiency, particularly at longer IR wavelengths (e.g. at or above 1000 nm) such as in the 1060-1100 nm range and specifically at 1064 nm. The detector 122 may be coupled 116 to the probe 110 via a fiber optic or other suitable optical coupling 118, with optional intervening optics 120 (e.g. filters). In some embodiments, tests were performed using photomultipliers such as a Hamamatsu NIR-PMT (data not shown), which has a slightly higher efficiency than the Excelitas photon counting APDs used in certain embodiments disclosed below. In other embodiments, superconducting nanowire detectors (e.g. WSi, NbN, etc.), which can be up to 95% efficient, were used for tests, as discussed below.

In various embodiments, one or more probes 202, 212, 222 (FIGS. 2A, 2B, and 2C) may be used with the source and detector to collect information from a tissue of a subject. The probe may be placed on or near a surface of the tissue (e.g. on the skin) such that light from the source impinges on the tissue surface and penetrates the tissue. Light emanating from the tissue as a result of the input light from the source is collected at one or more locations on the probe and directed to one or more detectors. The locations of the light input from the source and signal output to the detector on the probe are each separated by a distance which affects how deeply into the tissue the signal will come from, with increased distances generally providing signal from deeper into the tissue and closer distances providing signal from shallower portions of the tissue. In various embodiments, the distance may be 0.5 cm, 1.0 cm, 1.5 cm, 2.0 cm, 2.5 cm, or 3.0 cm, although other distances that are shorter, longer, or intermediate to these values are also possible.

Figure 2A:
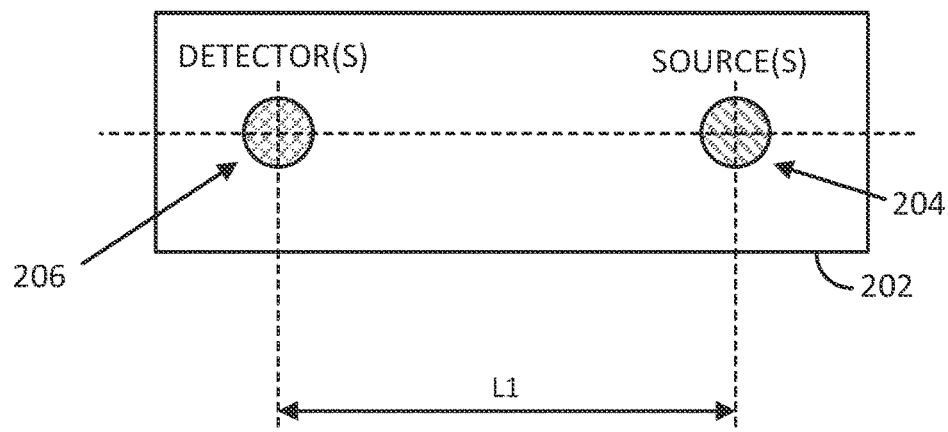
FIGS. 2A, 2B, and 2C show embodiments of probes that can be used with a DCS system such as that shown in FIG. 1A.
Figure 2B:
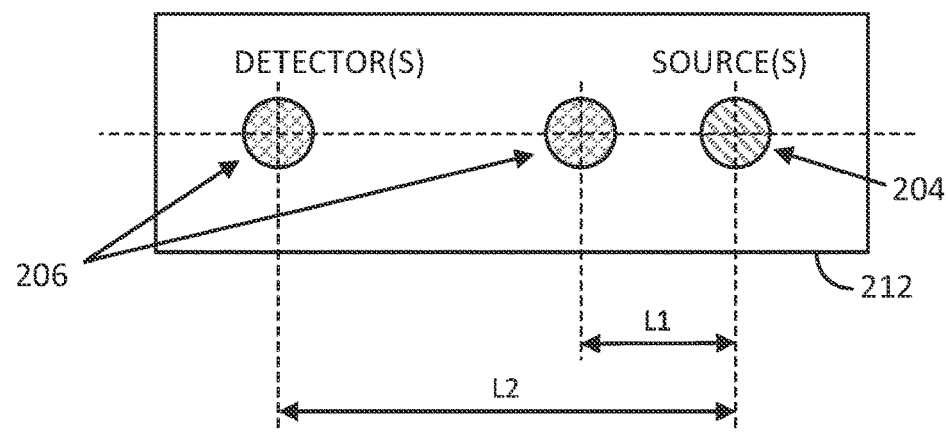

In some embodiments, a probe 202 may include a single input source location 204 and a single output detector location 206 separated by a distance L1 (FIG. 2A). In other embodiments, a probe 212 may include a single input source location 204 along with two or more detector locations 206, where the detector locations may be at varying distances L1, L2 from the source (closer and further away) to obtain signal from varying depths within the tissue (FIG. 2B). In various embodiments, the light from the different detector locations on the probe may be directed to different detector devices or, in the case of a detector having an array of elements, the light from each detector location may be directed to a different detector element (or group of elements) on the detector array. The source and detector locations may be aligned in a simple linear arrangement or may be located in a non-linear array, e.g. to provide information from different locations as well as depths within the tissue. One or more probes may be interfaced with a surface of a tissue by pressing the probe against the tissue surface (e.g. skin). In some embodiments the probe may be coupled to or integrated into a material that wraps around or attaches to a portion of the subject (e.g. a cap for the head, a band for the torso region, arm, or leg, or a clip for a digit such as a finger or toe) in order to keep the probe close to and/or in contact with the tissue surface for optimal recording, and the probe itself may be constructed of a flexible material (e.g. flexible plastic) that conforms to the surface of the tissue.

Figure 2C:
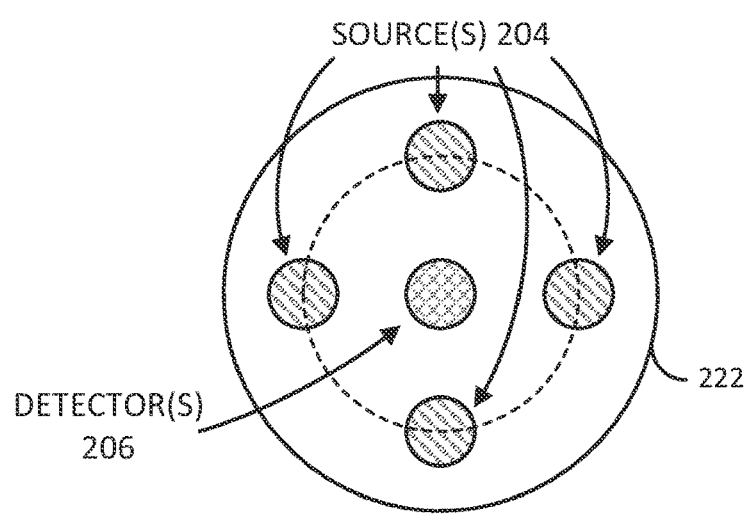

In general there are multiple detectors for each source on a probe to avoid complexities that could arise from having to separate light contributions arising from multiple sources. Nevertheless, in certain embodiments a single detector location 206 on a probe 222 may be associated with multiple source input locations 204, for example surrounding the detector 206 or arranged in other patterns relative to the detector location (FIG. 2C). In one particular embodiment, the input light directed to the source input locations 204 may be transmitted in a time-multiplexed manner, that is, light may be sent to one (or a subset of) source input location at a time rather than to all of the locations at the same time. By multiplexing the input light this helps maintain information regarding the spatial origin of the signal be being able to isolate the source from which detected photons originate and also ensures that the average input light power at each illumination location does not exceed a maximum permissible exposure level within a tissue area as prescribed by applicable standards. Various patterns of source input light delivery can be utilized which maintain illumination levels at or below acceptable levels.

In other embodiments, multiple probes may be associated with different tissues and different locations on the body of the subject to obtain additional information from the subject. These probes may each be associated with separate sources and detectors or may share one or more sources and/or detectors (including, for example, by directing light to different elements of a detector array), which may collect separate information from different locations within the body of the subject by multiplexing data collection, e.g. sequentially illuminating and detecting information from each of the probes in turn.

Figure 3A:
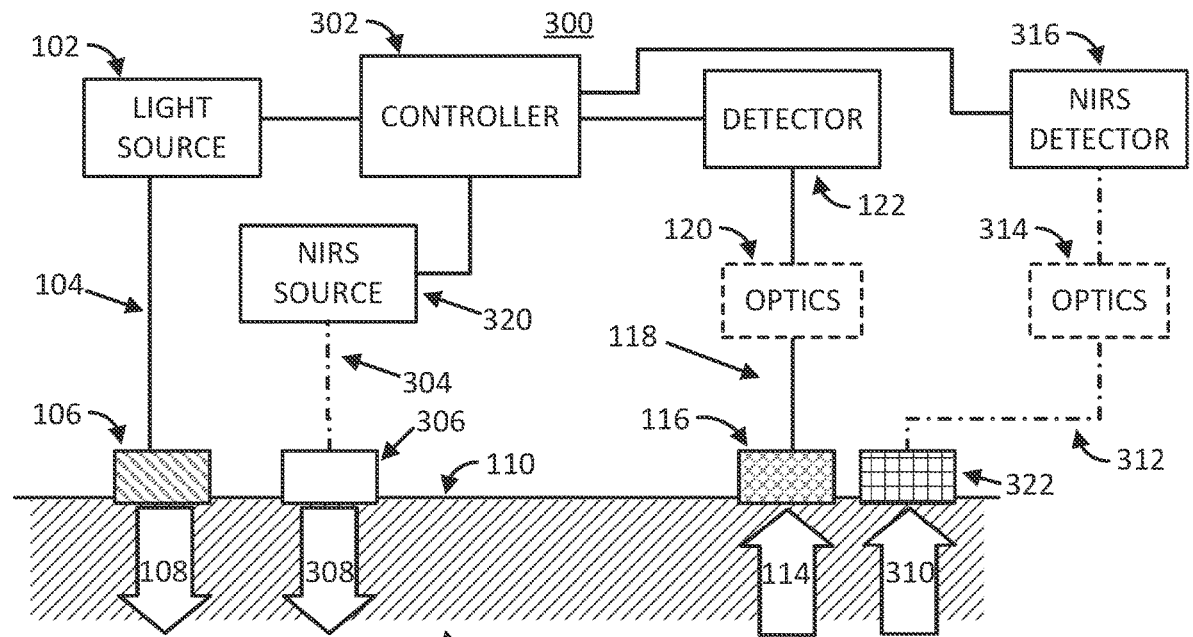
Figure 3B:
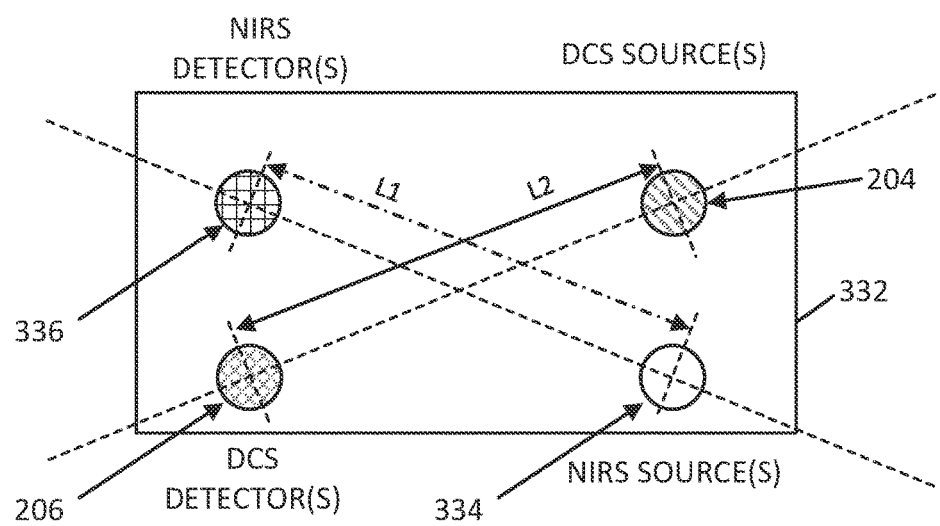
FIGS. 3B, 3C, and 3D show embodiments of probes to use with the combined DCS and NIRS system.

In some embodiments, the DCS system may be integrated with a system for performing NIRS, which permits additional data to be collected (e.g. to perform oximetry) which can then be combined with the DCS data. FIG. 3A shows a combined system 300 for obtaining DCS and NIRS measurements from a tissue. The combined system includes the DCS light source 102 and the DCS detector 122, each of which is coupled 106, 116 to different locations on a probe 110 separated by a particular distance (FIG. 3B). The system also includes a NIRS light source 320 and a NIRS detector 316 which are also coupled 306, 322 to different locations on the probe 110 and separated by a distance (FIG. 3B). The NIRS source 320 may be coupled by a fiber optic or other suitable optical coupling 304 to the probe 110 and the NIRS detector 316 may be coupled by a fiber optic or other suitable optical coupling 312 with optional intervening optics 314 (e.g. a filter). Light 108 from DCS light source enters the tissue 112 and light 308 from the NIRS source 320 enters the tissue 112 and the respective light exiting the tissue 114, 310 from each source is detected by the respective DCS detector 122 and NIRS detector 316 (FIG. 3A). A controller 302 is coupled to the respective sources 102, 320 and detectors 122, 316 and optionally to other components to coordinate data collection and/or processing. Although the system components in FIG. 3A are depicted as separate elements, in other embodiments the components may be combined in various configurations. For example, in some embodiments the DCS light source 102 and the NIRS light source 320 may connect to the probe 110 at the same location and the optical couplings may be bundled together or the light from both sources may be transmitted through a shared coupling (e.g. optical fiber) which may be split at an end away from the probe to make separate connections to each source.

In some embodiments, the DCS source 204 and NIRS source 334 probe locations may be arranged on a probe 332 as shown in FIG. 3B with the DCS detector 206 and NIRS detector 336 locations in a crossed pattern so that each modality illuminates and collects data from approximately the same region within the tissue. The NIRS source 320 may include multiple sources (e.g. laser diodes) each of which provides light of a particular wavelength within the optical window range of 650-900 nm (e.g. at one or more of 660, 670, 690, 705, 730, 780, 808, and 830 nm) in order to obtain spectral information that can be used to determine parameters such as levels of oxygenated hemoglobin in the tissue. The multiple sources may be directed into the same location on the probe (e.g. may be coupled together via fiber couplers) and may be illuminated sequentially in order to facilitate separating out the signal at each wavelength. In some embodiments, the DCS source 204 may also be used to obtain information for determining NIRS measurements, provided that the NIRS detector has sufficient sensitivity to the wavelength(s) of light from the DCS source 204.

Figure 3C:
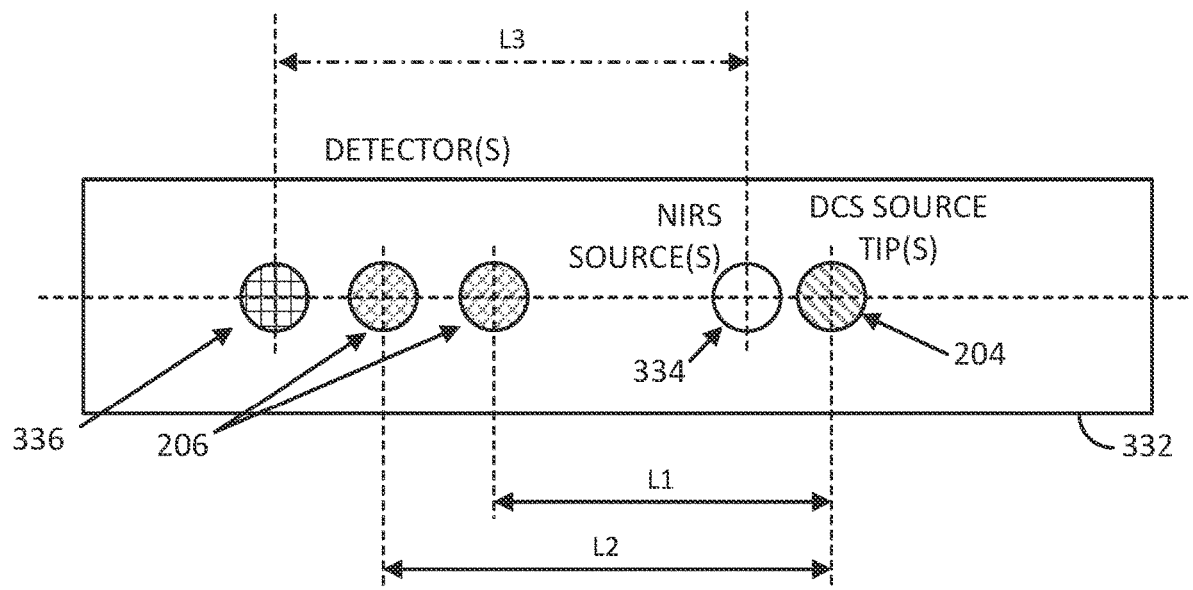
Figure 3D:
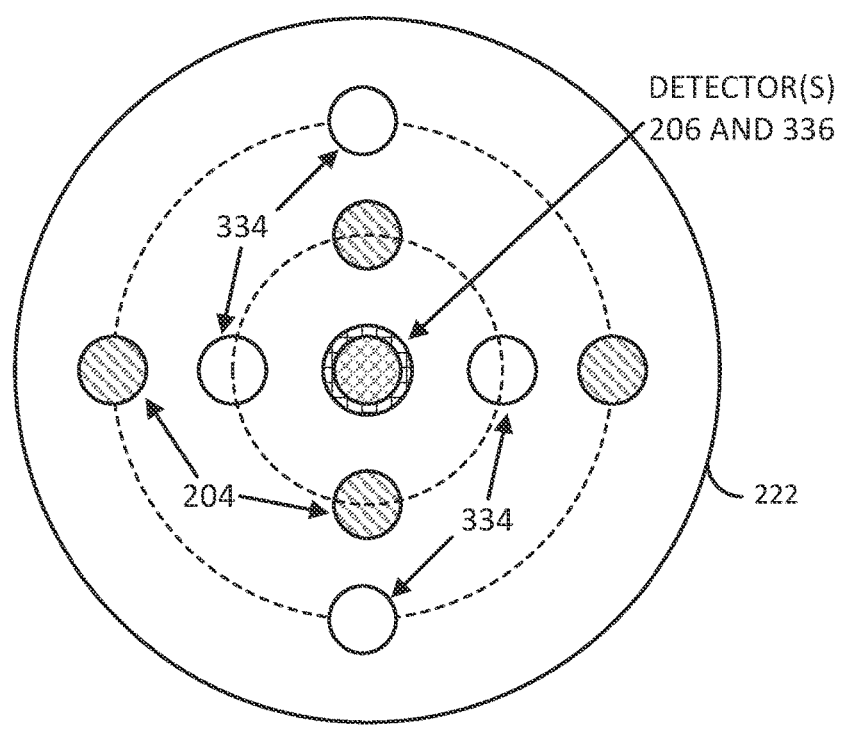

In some embodiments (FIG. 3C) a probe 332 may include the NIRS and DCS source and detector locations in a single linear array, including for example a NIRS source 334 separated from a NIRS detector 336 by a distance L3, and a DCS source 204 separated from two detectors 206 by distances of L1 and L2. In other embodiments (FIG. 3D) the DCS and NIRS sources 204, 334 may be arranged around a central location containing connections for the DCS and NIRS detectors 206, 336.

Using the longer IR wavelength DCS system with an NIRS system that uses shorter IR wavelengths, it is possible to produce a NIRS-DCS system which is improved relative to systems in which the DCS source also emits light in the 650-900 nm optical window range. By selecting suitable sources and detectors, the system is simplified and more efficient as it is not necessary to include wavelength filters (e.g. bandpass, low pass, or high pass filters) in front of the detectors. For example, in some embodiments a DCS detector may be selected which has little or no sensitivity at the wavelengths used for NIRS and conversely a NIRS detector may be selected which has little or no sensitivity at the wavelengths used for DCS. Accordingly, in one embodiment a NIRS light source may be selected which provides light of up to 900 nm, more particularly in a range of 650-900 nm, and a NIRS detector may be selected which has sensitivity in a range of up to 1050 nm, up to 1000 nm, or up to 900 nm. A DCS source may be selected which provides light of at least 1000 nm, in a range of 1000-1400 nm, of 1700 nm, in a range of 1060-1100 nm, or of 1064 nm. A DCS detector may be selected which has a sensitivity in a range of at least 1000 nm, at least 1000 nm, at least 1050 nm, or in a range of 1000-1700 nm. In various embodiments, the NIRS detector may be a photomultiplier tube (PMT), which has negligible sensitivity above 900 nm, or a silicon photodiode, which has negligible sensitivity above 1050 nm. The DCS detector may be a InP/InGaAs-based photodiode (e.g. a SPAD) or photodiode array, which has sensitivity in a range of 900-1700 nm.

As discussed further below, using longer IR wavelength illumination has an advantage of probing deeper into the tissue than the shorter IR or near-IR wavelengths of the optical window. Therefore, in some embodiments adjustments may be made to the system to account for differences in penetration depths of the different wavelengths of light, for example adjusting the distances between the source and detector locations on the probe for the DCS and NIRS modality so that approximately the same tissue depth is probed by each modality.

Attenuation Coefficient Considerations

Figure 4A:
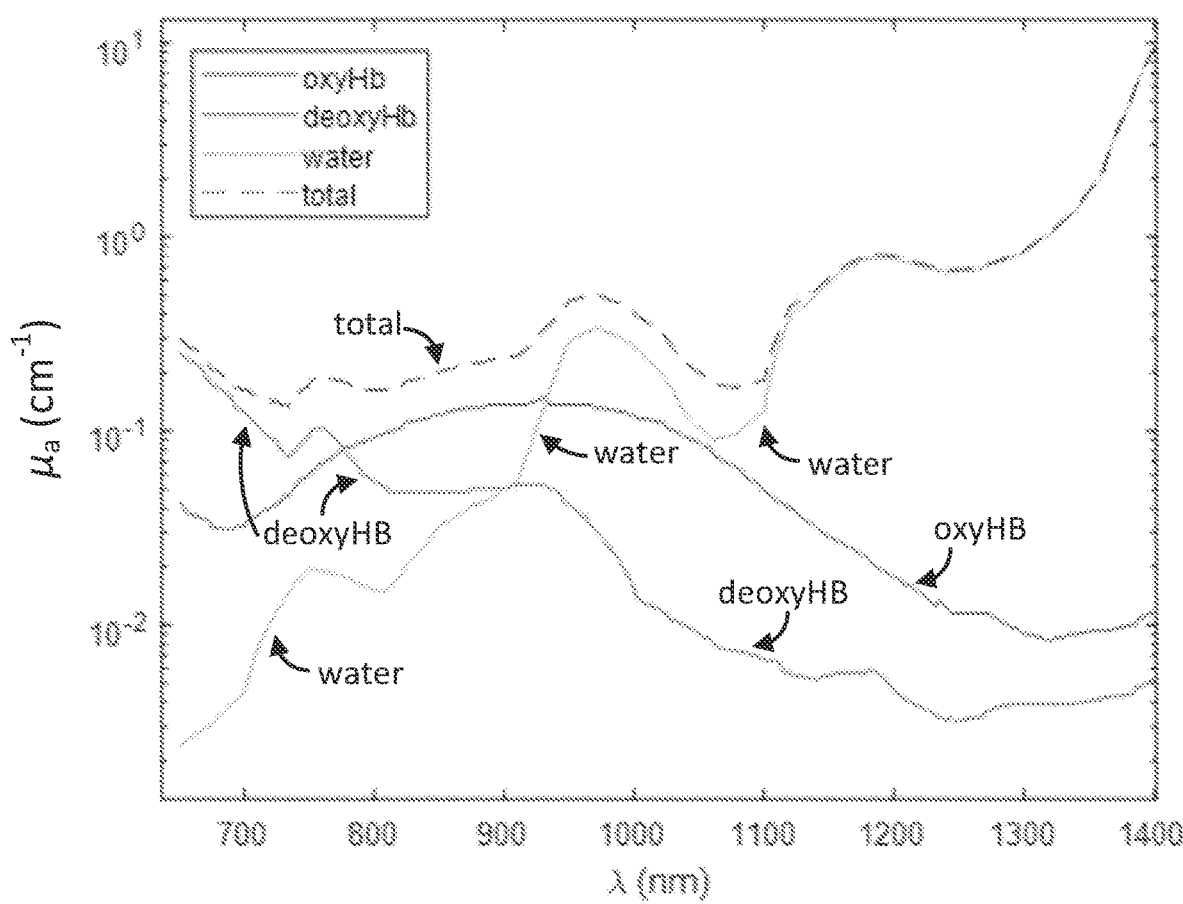
FIG. 4A shows a combined absorption spectrum of tissue containing 50 µM oxy-Hb, 30 µM deoxy-Hb, and 75% water.

Absorption in biological tissues is dominated by hemoglobin in the visible and near-infrared spectral region (400-900 nm) and by water for wavelengths above 900 nm. Between 1050-1100 nm water absorption has a local minimum (FIG. 4A), which offers an additional transmission window for deep tissue measurements. In fact, by considering typical tissue properties, i.e. hemoglobin concentration of ~80 µM, oxygenation ($SO_2$) of 62%, and water concentration of 75%, one obtains similar absorption coefficients of 1.5-2 $cm^{-1}$ at 700-850 nm and at 1064 nm.

Figure 4B:
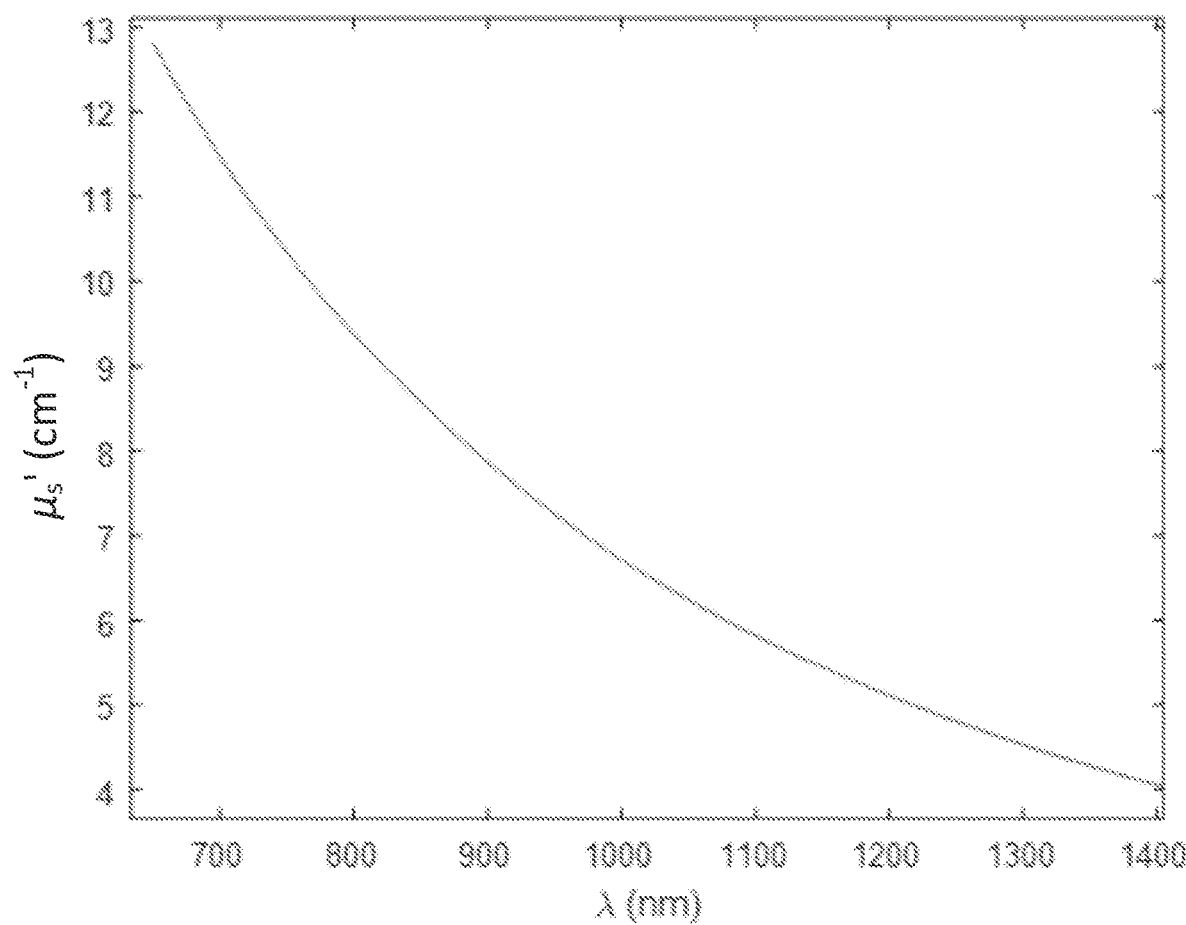
FIG. 4B shows a scattering spectrum of a tissue.
Figure 4C:
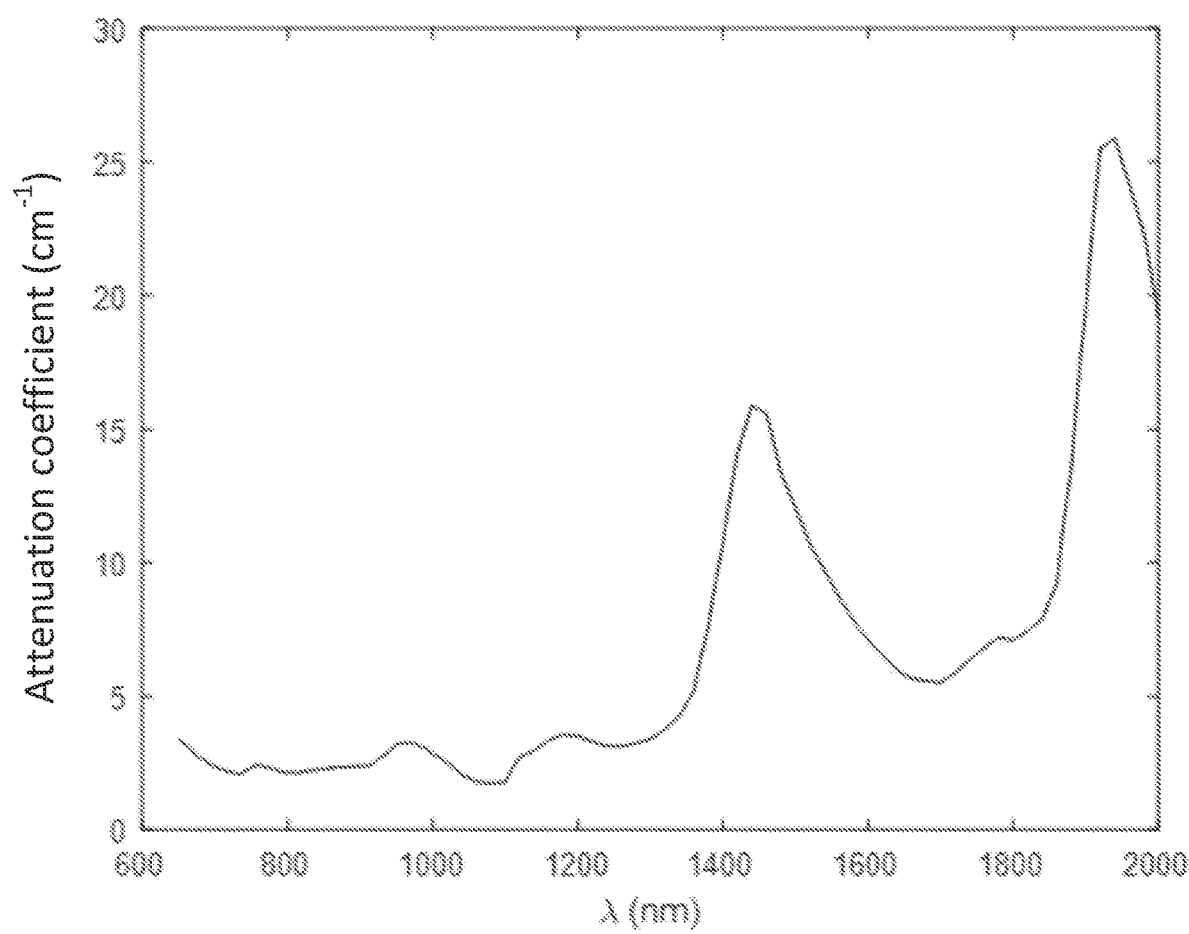
FIG. 4C shows an attenuation spectrum of a tissue.

The scattering coefficient ($\mu_s'$) decreases with wavelength and follows the empirical power law relationship of $\mu_s'(\lambda) = a\lambda^{-b}$, where a is the scaling factor and b is the scattering power. Assuming typical values for biological tissue of $\lambda_0 = 500$ nm, a=20 and b=1.5, at 1064 nm $\mu_s'$ is 30-40% lower than at 700-850 nm (FIG. 4B). As a result, the effective attenuation coefficient ($\mu_{eff}(\lambda) = \sqrt{3\mu_a(\mu_a + \mu_s')}$) (see FIG. 4C) for diffuse light at 1064 nm is 18-20% lower than at 850 and 765 nm, which are both typical wavelengths used for performing DCS.

While the relatively low absorption of hemoglobin poses problems for NIRS, for which the hemoglobin contrast is strongly reduced, this is not an issue for DCS. Instead, DCS contrast arises from the dynamic scattering of light by moving red blood cells, which remains substantial at longer wavelengths including at 1064 nm.

Figure 5:
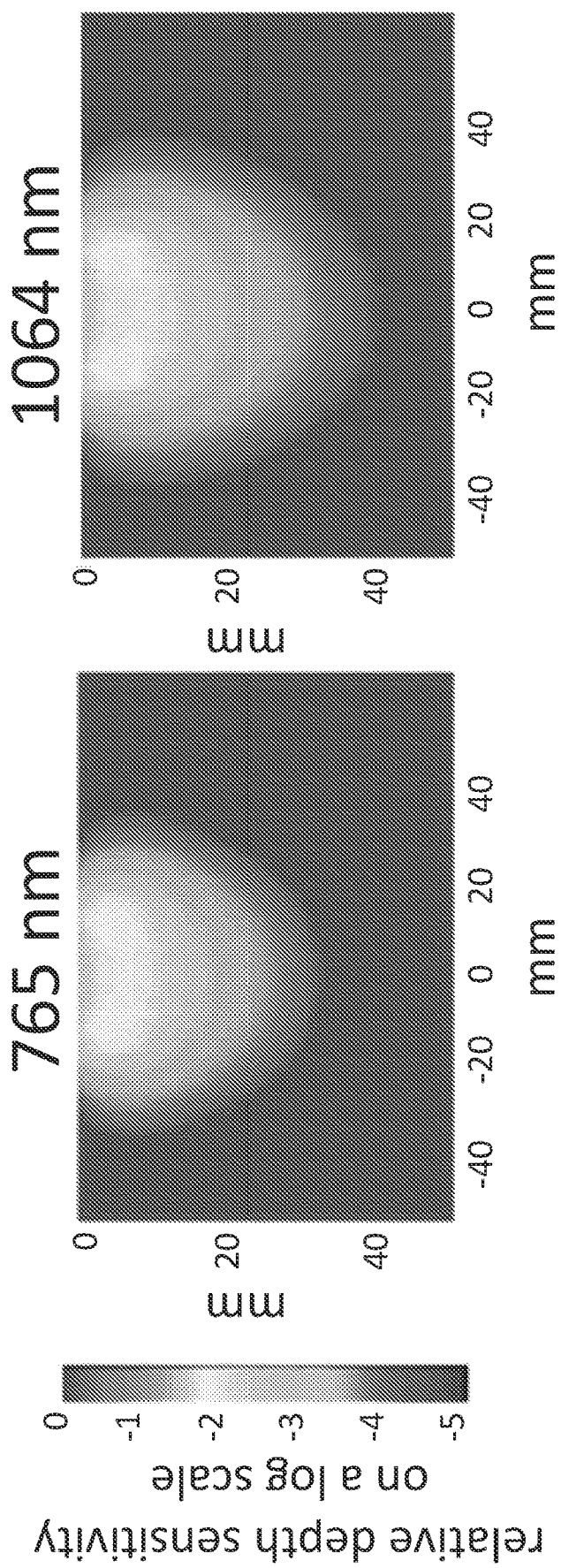
FIG. 5 shows simulated photon sensitivity profile results for 765 nm and 1064 nm.

The lower scattering and attenuation at longer wavelengths such as 1064 nm results in a higher penetration depth. To assess the depth penetration advantage at longer wavelengths, Monte Carlo simulations were performed in a two-layer slab model which describes the behavior of a transcranial measurement of an adult brain through a realistic layer of scalp and skull. The geometrical and optical properties of the layers are representative of a single upper extracerebral layer representing scalp and skull and a lower layer representing brain. In particular, the thickness of the top layer was set to 10 mm and the optical properties (reduced scattering ($\mu_s'$) and absorption ($\mu_a$) coefficients) were determined (see Table 1). The scattering for top and bottom layers was fixed to be 10 $cm^{-1}$ at 765 nm and 6 $cm^{-1}$ at 1064 nm. For the absorption coefficients at 765 nm, 0.075 $cm^{-1}$ was used for the top layer and 0.19 $cm^{-1}$ for the bottom layer; and at 1064 nm, 0.10 $cm^{-1}$ was used for the top layer and 0.17 $cm^{-1}$ for the bottom layer (see Table 1). FIG. 5 shows the photon sensitivity profile results for a source detector separation of 3 cm. By comparing the left and right panels of FIG. 5, it is evident that there is an increase in light penetration depth using 1064 nm light. By defining sensitivity to the brain as the fraction of the total signal attributable to the bottom layer, a gain of about 20% in brain sensitivity at 1064 nm was quantified with respect to 765 nm (see Table 1).

TABLE 1

| | 765 nm | | 1064 nm | |
| --- | --- | --- | --- | --- |
| | $\mu_a$ ($cm^{-1}$) | $\mu_s'$ ($cm^{-1}$) | $\mu_a$ ($cm^{-1}$) | $\mu_s'$ ($cm^{-1}$) |
| Top | 0.076 | 10 | 0.105 | 6 |
| Bottom | 0.188 | 10 | 0.173 | 6 |

Photon Budget Considerations

The lower attenuation at 1064 nm, in addition to increasing depth sensitivity, allows the detection of more photons. The relationship between the detected intensity at two wavelengths is proportional to the corresponding attenuation coefficients, $$\frac{I_{\lambda_1}}{I_{\lambda_0}} = e^{\left(\frac{\mu_{eff_{\lambda_0}} - \mu_{eff_{\lambda_1}}}{\mu_{eff_{\lambda_0}}}\right)r},$$

and for r=3 cm, since $\mu_{eff_{765}}$=2.3 cm$^{-1}$ and $\mu_{eff_{1064}}$=1.8 cm$^{-1}$, the number of photons collected at 1064 nm is 1.9 times higher than at 765 nm.

In addition, comparing the ANSI standards limits for safe skin exposure at 1064 nm versus 765 nm (pursuant to ANSI Z136.1-2000), one can deliver four times more energy (i.e. 100 mW at 1064 nm vs. 25 mW at 765 nm, for a >1 mm$^2$ illumination area).

Finally, photons at longer wavelengths carry less energy, $$E_{\lambda_1} = E_{\lambda_0} \cdot \frac{\lambda_0}{\lambda_1},$$

so that, given two equal energy doses of photons at 765 nm and 1064 nm, at 1064 nm there are 1.4 times more photons than at 765 nm.

Multiplying together these three factors (namely, lower effective attenuation, higher maximum permissible exposure (MPE), and more photons per unit energy), by illuminating with light at 1064 nm one ends up with at least 10 times more photons at the DCS detector than when illuminating at 765 nm. This is a considerable gain since the number of photons directly impacts the measurement signal to noise ratio (SNR).

Intensity Autocorrelation Function Decay Considerations

The measured temporal intensity autocorrelation function ($g_2$) used with DCS to fit for blood flow index (BF$_i$) depends on the motions of red blood cells, which is dependent on wavelength and scattering:

$$g_2(\tau) = 1 + \beta\left[\exp\left(-(3\mu_3\mu_s' + P_{RBC} <\Delta r^2(\tau)> \mu_s'^2\pi/\lambda^2)^{1/2}|\rho|\right)\right]^2$$

As scattering at 1064 nm is 30-40% lower than at 765 nm and the wavelength is higher, there is a slower $g_2$ decay time (>1 μs) which leads to further improved SNR in the temporal decay region of interest and thus a less noisy BF$_i$ fit.

Figure 6B:
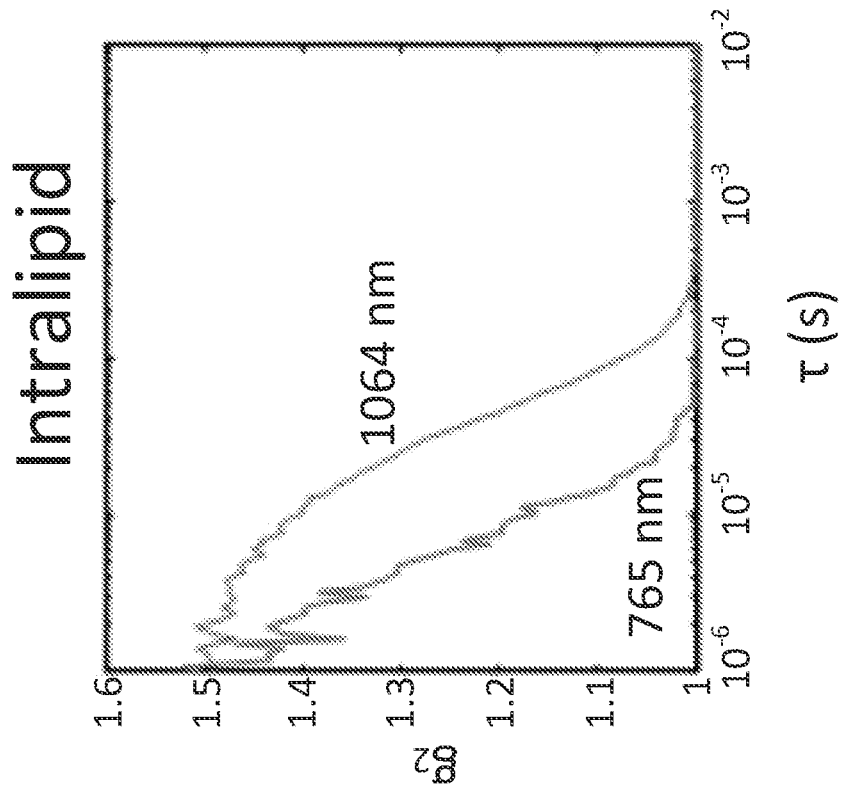
FIGS. 6A, 6B, and 6C show a temporal autocorrelation function measured at 765 nm and 1064 nm in a) silicone oil (FIG. 6A), b) intralipid (FIG. 6B), and c) a human forehead (FIG. 6C)
Figure 6A:
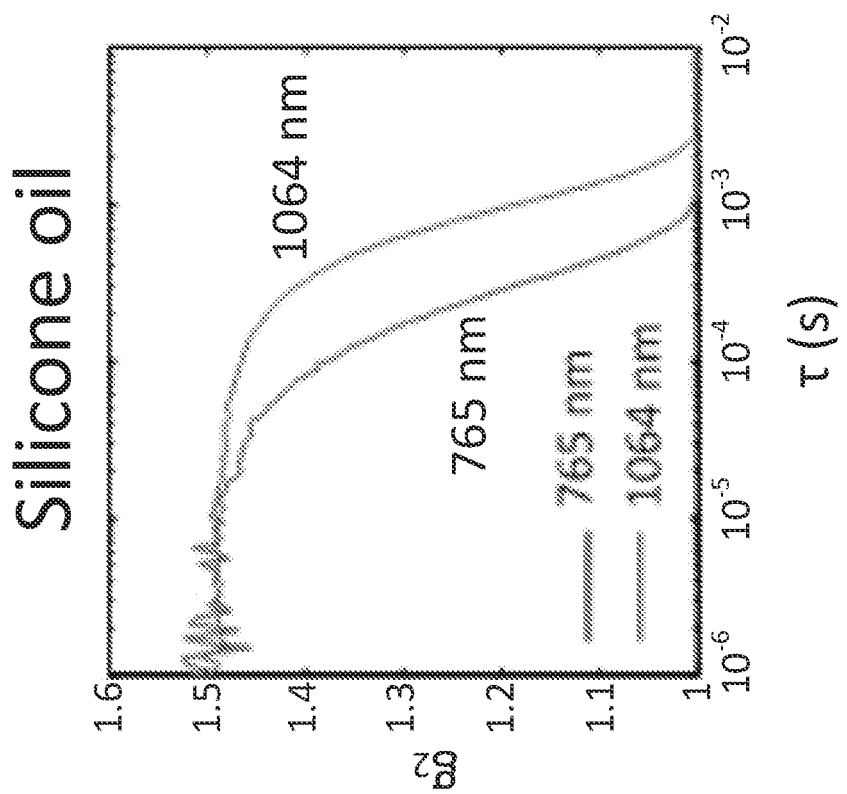
Figure 6C:
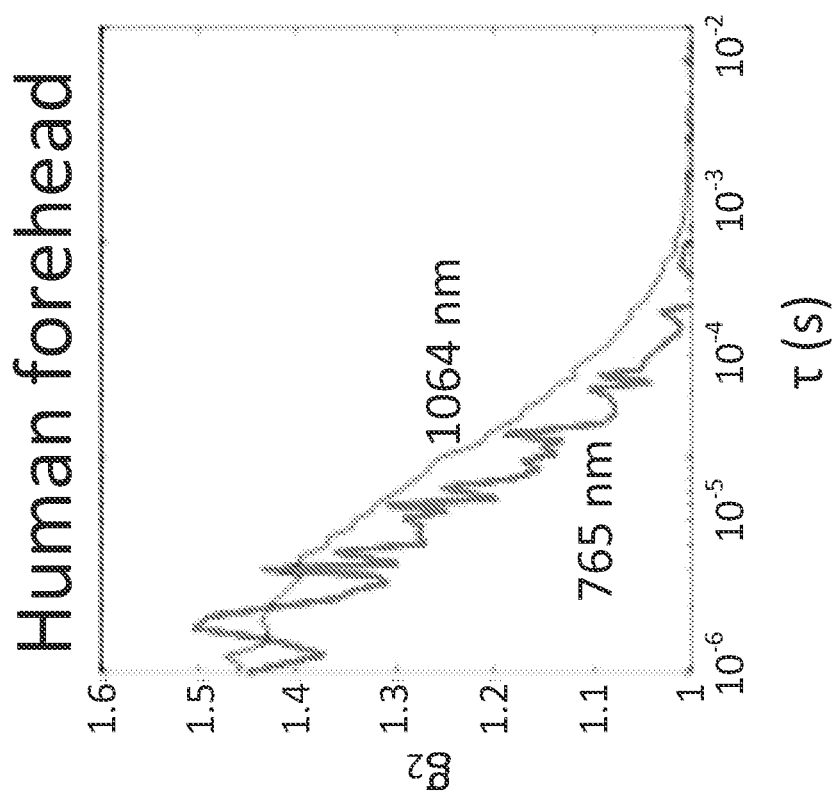

FIGS. 6A, 6B, and 6C show a temporal autocorrelation function measured at 765 nm and 1064 nm in a) silicone oil (FIG. 6A), b) intralipid (FIG. 6B), and c) a human forehead (FIG. 6C). The decay of $g_2$ is much slower for the two homogeneous liquid phantoms at 1064 nm because of the lower scattering and longer wavelength λ. In the human forehead the difference between the $g_2$ values at the two wavelengths is smaller because at 1064 nm, light penetrates deeper and is more sensitive to the brain than light at 765 nm, which is more sensitive to the scalp. Blood flow in the brain is higher, resulting in a similar decay of $g_2$ at the two wavelengths.

If BFi is calculated assuming a 2 cm$^{-1}$ lower scattering at 1064 nm, one obtains the same BFi in the phantoms and a BFi 50% higher at 1064 nm than at 765 nm in the forehead.

DCS Systems

In some embodiments, DCS measurements were made using a custom-built multicolor DCS system (Tamborini et al., Neurophotonics 5(1), 011015 (2017), which is incorporated by reference herein in its entirety) in which one of the sources was replaced with a laser at 1064 nm. Specifically, the monolithic distributed Bragg reflector (DBR) lasers at 765 and 850 nm ((PHxxxDBR series, by Photodigm Inc) were retained and the laser at 808 nm was replaced with a DBR laser emitting at 1064 nm (PH1064DBR). The same custom circuitry was used to drive this laser, without fast multiplexing between the three lasers, allowing operation at a manually-selected wavelength each time. For detectors, this system uses single-photon avalanche diodes (SPCM-850-14-FC, by Excelitas Technologies) which have a good photon detection efficiency (PDE) at 765 nm and 850 nm (64% and 54%, respectively), but only 3% efficiency at 1064 nm. The low PDE of the silicon detectors at 1064 was a limiting factor on the choice of source-detector separation and was taken into account when comparing performances at different wavelengths.

Phantom Measurements

Figure 7C:
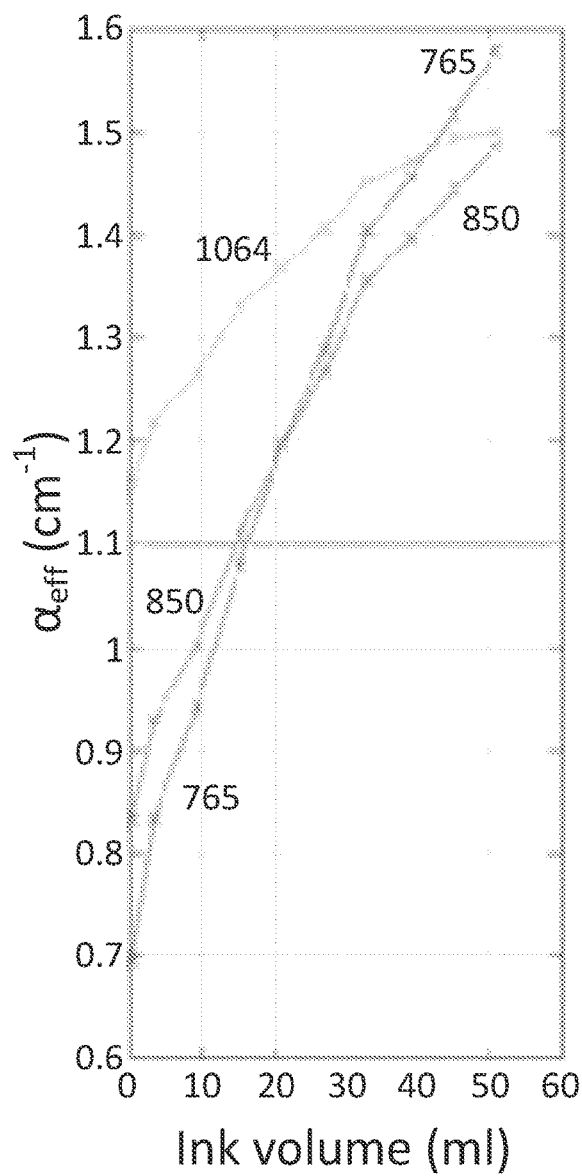
Figure 7D:
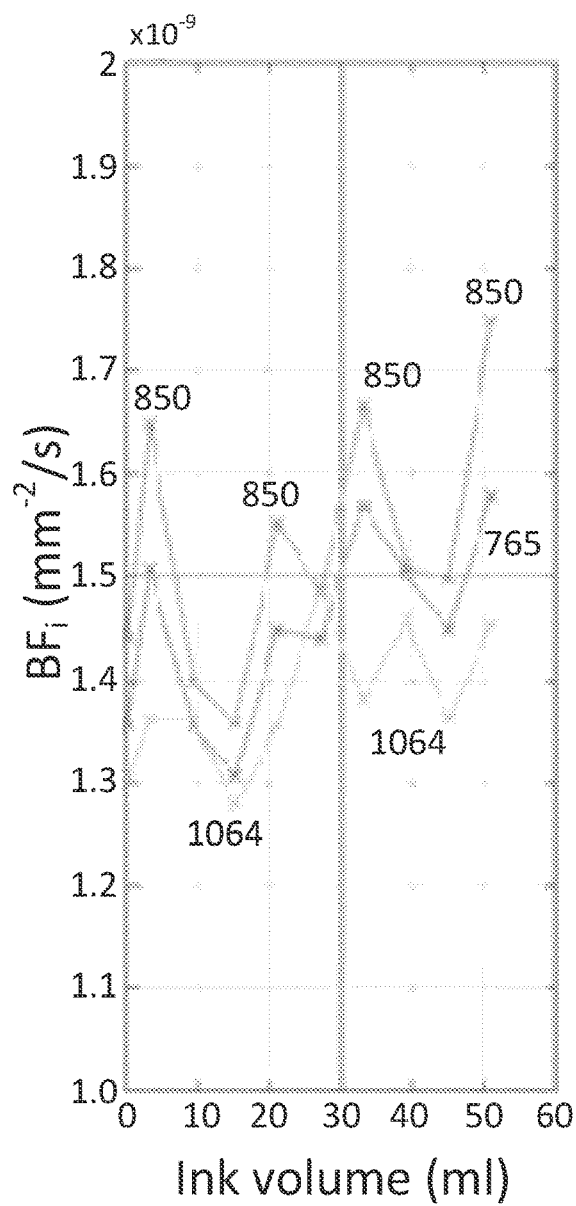

FIGS. 7A-7D show the results of using the above system with liquid phantoms based on ink titrations, showing $\alpha_a$ (FIG. 7A), $\alpha_s$ (FIG. 7B), $\alpha_{eff}$ (FIG. 7C), and BFi (FIG. 7D). Because the absorption spectrum of ink does not decrease as a function of wavelength as much as hemoglobin, relatively high amounts of ink were used to compensate for water absorption at 1064 nm in order to obtain comparable attenuation as hemoglobin at this wavelength. These results show that at the different wavelengths, the same BFi is obtained (see FIG. 7D) despite the differences in scattering and absorption.

Human Subject Measurements

Figure 8:
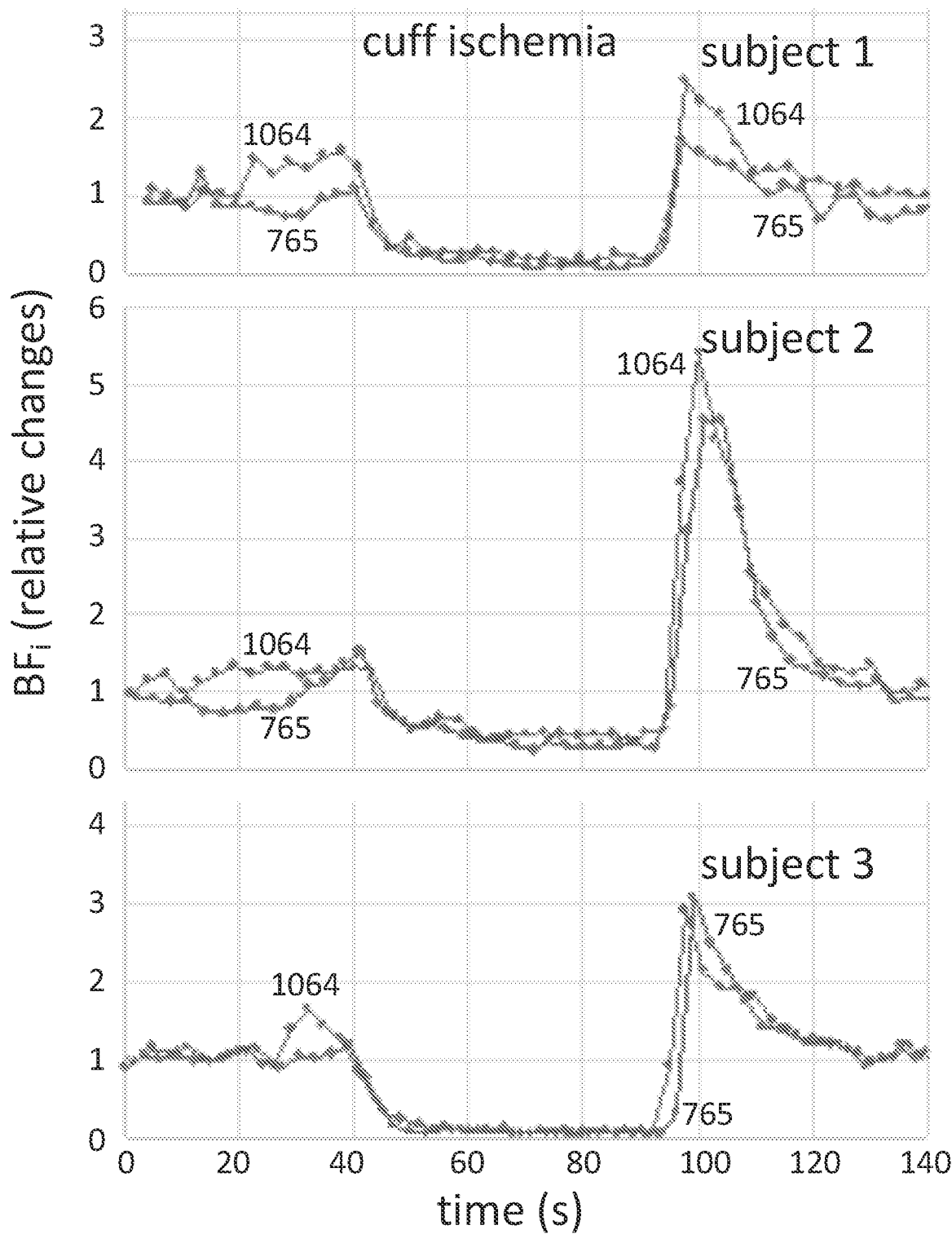
FIG. 8 shows the results of an in vivo demonstration of performing DCS using light with a wavelength of 765 nm vs light with a wavelength of 1064 nm.

FIG. 8 shows the results of the first in vivo demonstration of performing DCS using light with a wavelength of 765 nm vs light with a wavelength of 1064 nm. A probe having a 1 cm source-detector separation distance was used for this exemplary test because of the low signal at 1064 nm, i.e. due to the low (3%) single photon avalanche diode (SPAD) efficiency. As noted above, this test system used Excelitas detectors having very low detection efficiency at 1064 nm.

Nevertheless, these results showed: comparable relative BFi during repeated occlusions in the same subjects (differences within a given subject being due to non-simultaneous measurements being made); consistent differences across subjects; and that a difference of ~2 cm$^{-1}$ in scattering is needed to match BFi absolute values.

In some embodiments, superconducting nanowire detectors (SNSPD) having 90% photon detection efficiency were used, which permitted collecting measurements at larger source-detector separations.

CW-DCS at 1064 nm Using a SNSPD

Continuous Wave DCS (CW-DCS) was performed on human subjects at 1064 nm using a superconducting nanowire single photon detector (SNSPD). The high PDE (~80%) of these detectors enabled DCS measurements to be made using larger source-detector separation distances (up to 3 cm) at 1064 nm than were used with the low-efficiency Excelitas SPAD detectors.

Pressure modulation on the forehead (see FIG. 9, top) was used to reduce blood flow in the skin region under the detector. In particular, by pressing the optical probe on the forehead blood flow to the skin was blocked in the region under the probe, resulting in a lower BFi in the scalp while leaving BFi in the brain unaffected.

Figure 9:
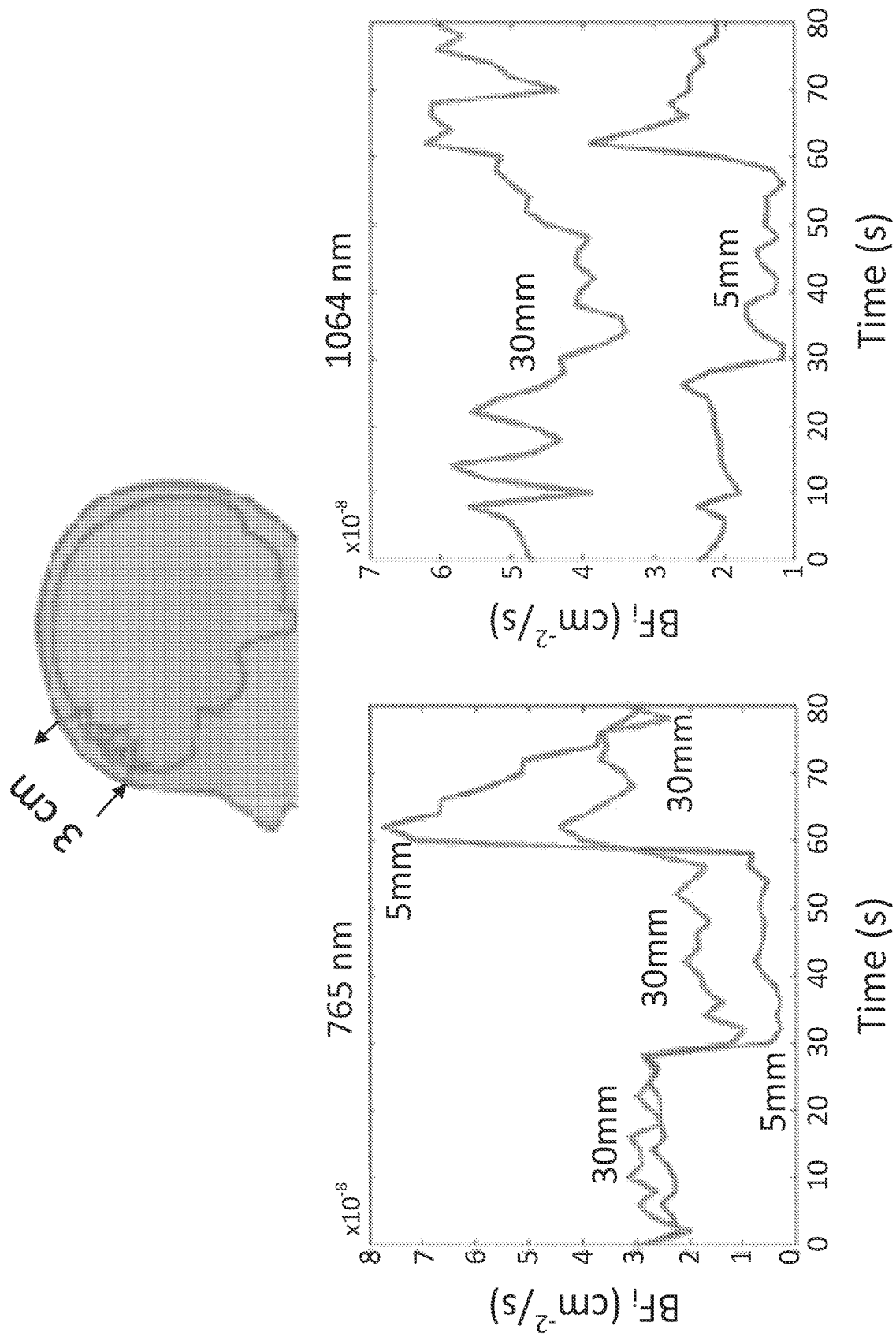
FIG. 9 shows measurements of BFi made with CW-DCS at 765 nm and 1064 nm with pressure applied to the forehead during part of the measurement to reduce skin blood flow.

At a short source-detector separation distance (5 mm), BFi was only measured in the scalp (FIG. 9). During pressure modulation (from approximately 30 sec to 60 sec), BFi at 5 mm (blue curves) decreases almost to zero. Using a probe with a 3 cm source-detector separation distance (red curves), one would predict a smaller decrease in BFi while pressure is applied if the signal is primarily sensitive to the brain. As seen in FIG. 9, contamination of the 3 cm distance signal with scalp blood flow is substantially smaller at 1064 nm than at 765 nm, both because of the higher penetration at 1064 nm as well as the higher sensitivity at this wavelength to brain tissue.

Figure 10:
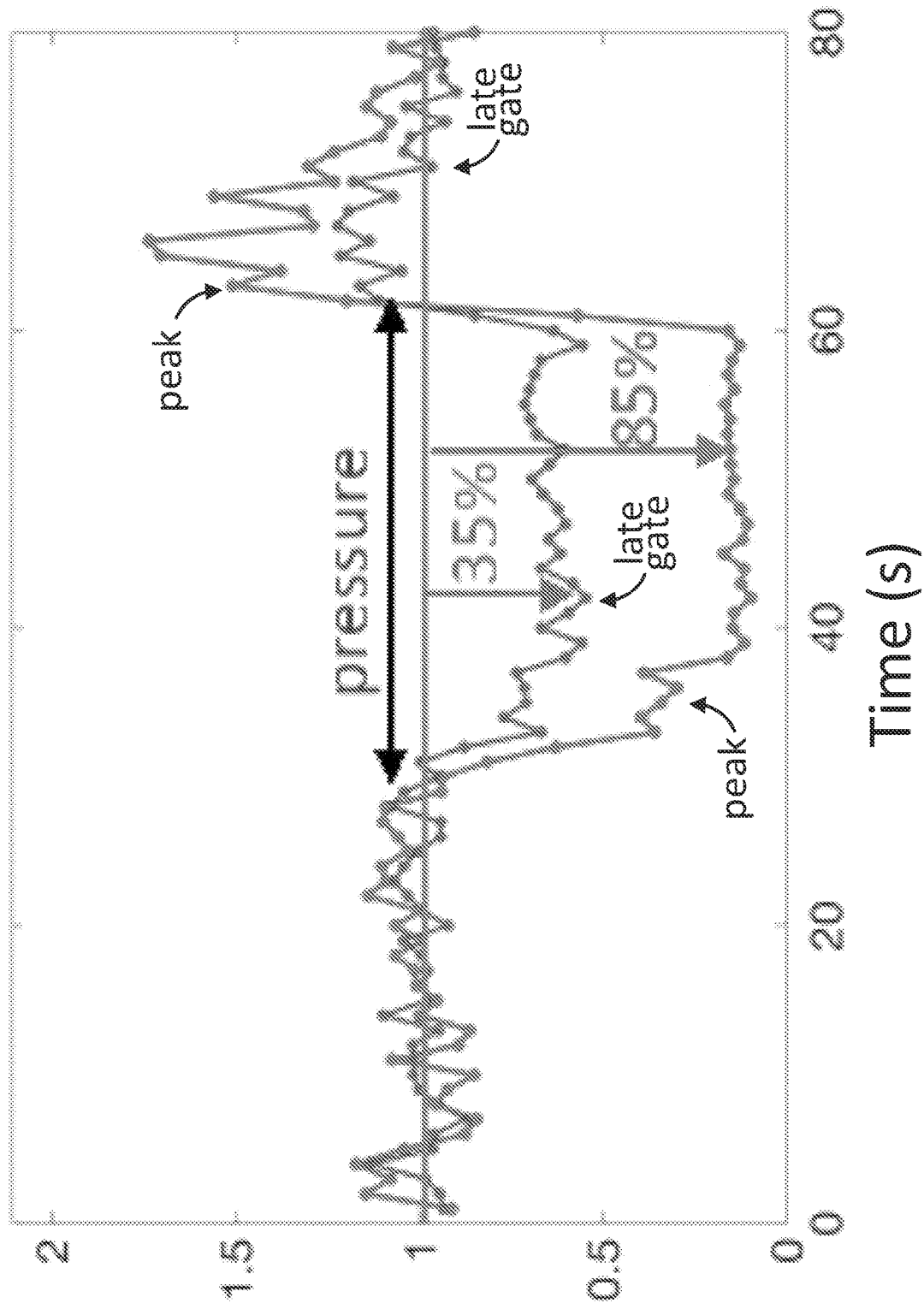
FIG. 10 shows measurements of rBFi made using TD-DCS at 1064 nm with pressure applied to the forehead during part of the measurement to reduce skin blood flow.

FIG. 10 shows similar pressure modulation measurements that were performed using time-domain (TD) DCS at 1064 nm. In this instance, instead of using a probe having a larger source-detector separation distance to increase sensitivity to brain tissue, we have used late-arriving photons (late gates) where the peak corresponds to short separations in a CW measurement. In addition, in this case at 1064 nm the sensitivity to brain tissue is higher than using typical DCS wavelengths.

Thus, light with a wavelength of 1064 nm can be used for CW-DCS, TD-DCS, interferometric DCS (iDCS and iDWS), heterodyne DCS, and acousto-optic modulated DCS, while maintaining the same advantages of higher penetration and higher photon budget.

The present disclosure has described one or more preferred embodiments, and it should be appreciated that many equivalents, alternatives, variations, and modifications, aside from those expressly stated, are possible and within the scope of the invention.

What is claimed is:

1. An apparatus, comprising:
   a probe to interface with a surface of a tissue;
   a first light source optically coupled to the probe,
      the first light source providing light of up to 900 nm into the tissue;
   a second light source optically coupled to the probe,
      the second light source providing light of at least 1000 nm into the tissue;
   a first detector optically coupled to the probe,
      the first detector to detect light scattered in the tissue from the first light source, and
      the first detector having a light sensitivity in a range of up to 900 nm;
   a second detector optically coupled to the probe,
      the second detector to detect light scattered in the tissue from the second light source, and
      the second detector having a light sensitivity in a range of at least 1000 nm; and
   a processor coupled to the first detector and the second detector, the processor to:
      receive a first signal from the first detector corresponding to the detected light from the first light source,
      receive a second signal from the second detector corresponding to the detected light from the second light source, and
      determine a blood flow measurement from the region of interest based on the first signal and the second signal.

2. The apparatus of claim 1, wherein the first light source provides light in a range of 650-900 nm.

3. The apparatus of claim 2, wherein the first light source comprises a plurality of first light sources,
   wherein each of the plurality of first light sources generates light of a particular wavelength.

4. The apparatus of claim 1, wherein the second light source provides light in a range of 1000-1400 nm.

5. The apparatus of claim 1, wherein the first source is coupled to the probe at a first probe location,
   wherein the first detector is coupled to the probe at a second probe location, and
   wherein the first probe location and the second probe location are separated by a first distance.

6. The apparatus of claim 5, wherein the first distance is 3 cm.

7. The apparatus of claim 1, wherein the second source is coupled to the probe at a third probe location,
   wherein the second detector is coupled to the probe at a fourth probe location, and
   wherein the third probe location and the fourth probe location are separated by a second distance.

8. The apparatus of claim 7, wherein the second distance is 3 cm.

9. The apparatus of claim 1, wherein the first detector comprises at least one of a photomultiplier tube or a silicon photodiode.

10. The apparatus of claim 1, wherein the second detector comprises a InP/InGaAs detector.

11. The apparatus of claim 10, wherein the second detector comprises a single photon avalanche photodiode (SPAD).

12. The apparatus of claim 1, wherein the second detector comprises a superconducting nanowire detector.

13. A method, comprising:
    directing, using a first light source, light of up to 900 nm into a tissue,
       the first light source optically coupled to a probe,
          the probe interfaced with a surface of the tissue;
    directing, using a second light source, light of at least 1000 nm into the tissue,
       the second light source optically coupled to the probe,
          the probe interfaced with a surface of the tissue;
    detecting, using a first detector, light based on scattering of light from the first light source in the tissue,
       the first detector optically coupled to the probe, and
       the first detector having a light sensitivity in a range of up to 900 nm;
    detecting, using a second detector, light based on scattering of light from the second light source in the tissue,
       the second detector optically coupled to the probe, and
       the second detector having a light sensitivity in a range of at least 1000 nm;
    receiving, by a processor, a first signal from the first detector corresponding to the detected light from the first light source;
    receiving, by the processor, a second signal from the second detector corresponding to the detected light from the second light source; and
    determining, by the processor, a blood flow measurement from the region of interest based on the first signal and the second signal.

14. The method of claim 13, wherein the first light source provides light in a range of 650-900 nm.

15. The method of claim 14, wherein the first light source comprises a plurality of first light sources,
    wherein each of the plurality of first light sources generates light of a particular wavelength.

16. The method of claim 13, wherein the second light source provides light in a range of 1000-1400 nm.

17. The method of claim 13, wherein the first source is coupled to the probe at a first probe location,
    wherein the first detector is coupled to the probe at a second probe location, and
    wherein the first probe location and the second probe location are separated by a first distance.

18. The method of claim 17, wherein the first distance is 3 cm.

19. The method of claim 13, wherein the second source is coupled to the probe at a third probe location, wherein the second detector is coupled to the probe at a fourth probe location, and wherein the third probe location and the fourth probe location are separated by a second distance.

20. The method of claim 19, wherein the second distance is 3 cm.

21. The method of claim 13, wherein the first detector comprises at least one of a photomultiplier tube or a silicon photodiode.

22. The method of claim 13, wherein the second detector comprises a InP/InGaAs detector.

23. The method of claim 22, wherein the second detector comprises a single photon avalanche photodiode (SPAD).

24. The method of claim 13, wherein the second detector comprises a superconducting nanowire detector.

\* \* \* \* \*